US010697947B1

(12) United States Patent
Armitage

(10) Patent No.: US 10,697,947 B1
(45) Date of Patent: Jun. 30, 2020

(54) APPARATUS AND METHODS FOR REDUCING FUGITIVE GAS EMISSIONS AT OIL FACILITIES

(71) Applicant: Project Canary, Inc., Denver, CO (US)

(72) Inventor: David L. Armitage, Denver, CO (US)

(73) Assignee: PROJECT CANARY, INC., Denver, CO (US)

(*) Notice: Subject to any disclaimer, the term of this patent is extended or adjusted under 35 U.S.C. 154(b) by 0 days.

(21) Appl. No.: 16/517,586

(22) Filed: Jul. 20, 2019

Related U.S. Application Data

(60) Provisional application No. 62/851,563, filed on May 22, 2019, provisional application No. 62/795,608, filed on Jan. 23, 2019.

(51) Int. Cl.
*G01N 33/00* (2006.01)
*H02S 20/10* (2014.01)
*A01K 31/14* (2006.01)
*E21B 41/00* (2006.01)
*G08B 21/16* (2006.01)

(52) U.S. Cl.
CPC ......... *G01N 33/0009* (2013.01); *A01K 31/14* (2013.01); *E21B 41/00* (2013.01); *G08B 21/16* (2013.01); *H02S 20/10* (2014.12)

(58) Field of Classification Search
CPC .... G01N 33/0009; H02S 20/10; G08B 21/16; E21B 41/00; A01K 31/14
See application file for complete search history.

(56) References Cited

U.S. PATENT DOCUMENTS

| | | | |
|---|---|---|---|
| 3,662,171 A | 5/1972 | Brengman et al. | |
| 3,780,566 A | 12/1973 | Smith et al. | |
| 4,135,092 A | 1/1979 | Milly | |
| 4,551,719 A | 11/1985 | Carlin et al. | |
| 5,132,968 A | 7/1992 | Cephus | |
| 5,281,816 A | 1/1994 | Jacobson et al. | |
| 5,406,265 A | 4/1995 | Trozzo et al. | |
| 5,568,121 A | 10/1996 | Lamensdorf | |
| 5,604,298 A * | 2/1997 | Dosoretz ................ | G01M 3/20 73/23.2 |
| 6,061,141 A | 5/2000 | Goldenberg et al. | |
| 6,114,964 A | 9/2000 | Fasano | |

(Continued)

FOREIGN PATENT DOCUMENTS

| | | |
|---|---|---|
| CH | 703014 A2 | 10/2011 |
| CN | 107782374 A | 3/2018 |

(Continued)

OTHER PUBLICATIONS

United States Environmental Protection Agency, "Tracking Emissions Using New Fenceline Monitoring Technology", published Jun. 18, 2018, <https://www.epa.gov/sciencematters/tracking-emissions-using-new-fenceline-monitoring-technology>, retrieved from the Internet Jul. 19, 2019, 3 pages.

(Continued)

*Primary Examiner* — Ryan W Sherwin
(74) *Attorney, Agent, or Firm* — Stephen Katsaros

(57) ABSTRACT

Apparatus and methods for detecting and reporting pollution at an oil facility are disclosed. The technology utilizes a logic control system to read from a pollution sensor and present the sensed data as a pollutant from a leak. The pollution leakage can be further managed and reduced.

20 Claims, 31 Drawing Sheets

(56) References Cited

U.S. PATENT DOCUMENTS

| | | |
|---|---|---|
| 6,169,488 B1 | 1/2001 | Ketler |
| 6,252,510 B1 | 6/2001 | Dungan |
| 6,259,956 B1 | 7/2001 | Myers et al. |
| 6,317,029 B1 | 11/2001 | Fleeter |
| 6,415,646 B1 | 7/2002 | Kessel et al. |
| 6,490,530 B1 | 12/2002 | Wyatt |
| 6,794,991 B2 | 9/2004 | Dungan |
| 7,075,653 B1 | 7/2006 | Rutherford |
| 7,080,544 B2 | 7/2006 | Stepanik et al. |
| 8,485,019 B2 | 7/2013 | Groves |
| 8,510,059 B2 | 8/2013 | Prince |
| 8,712,335 B2 | 4/2014 | Mathur et al. |
| 8,714,035 B2 | 5/2014 | Mihaylav et al. |
| 8,949,037 B2 | 2/2015 | Prince et al. |
| 9,018,963 B2 | 4/2015 | Sim et al. |
| 9,075,016 B2 | 7/2015 | Groves |
| 9,188,503 B2 | 11/2015 | Kloepper et al. |
| 9,754,472 B2 | 9/2017 | Johnson et al. |
| 9,878,656 B2 | 1/2018 | Gergets et al. |
| 9,978,251 B2 | 5/2018 | Gonia et al. |
| 10,021,466 B2 | 7/2018 | Guglielmo et al. |
| 10,089,849 B2 | 10/2018 | Liu et al. |
| 10,119,890 B2 | 11/2018 | Massengale et al. |
| 10,190,976 B2 | 1/2019 | Waxman et al. |
| 10,210,738 B2 | 2/2019 | Johnson, Jr. et al. |
| D842,134 S | 3/2019 | Doi et al. |
| 2001/0040509 A1 | 11/2001 | Dungan |
| 2004/0056771 A1* | 3/2004 | Dungan ............ G01N 33/0075 340/632 |
| 2008/0281528 A1 | 11/2008 | Relle, Jr. |
| 2010/0295673 A1 | 11/2010 | Ahmad |
| 2011/0219891 A1 | 9/2011 | Mihaylov et al. |
| 2012/0012066 A1 | 1/2012 | Beery et al. |
| 2012/0109583 A1 | 5/2012 | Bartlett et al. |
| 2012/0227983 A1* | 9/2012 | Lymberopoulos ...... E21B 34/02 166/373 |
| 2015/0185194 A1 | 7/2015 | Prince et al. |
| 2017/0130480 A1 | 5/2017 | Perkins |
| 2017/0336281 A1 | 11/2017 | Waxman et al. |
| 2018/0266933 A1 | 9/2018 | Tamraz et al. |
| 2019/0110444 A1* | 4/2019 | Boehm ................. A01K 31/14 |

FOREIGN PATENT DOCUMENTS

| | | |
|---|---|---|
| CN | 109521162 A | 3/2019 |
| EP | 2687844 A2 | 1/2014 |

OTHER PUBLICATIONS

United States Environmental Protection Agency, "SPod Fenceline Sensors Under Development", <https://www.epa.gov/sites/production/files/2016-04/documents/spod_fact_sheet.pdf>, retrieved from the Internet Jul. 19, 2019, 1 page.

JJS Technical Services, "BW Technologies Rig Rat III Gas Detector (Non-Wireless Version)", <https://www.jjstech.com/rr-3000s.html>, retrieved from the Internet Jul. 19, 2019, 3 pages.

Collier-Oxandale, et al., "Understanding the ability of low-cost MOx sensors to quantify ambient VOCs", Atmospheric Measurement Techniques, Mar. 5, 2019, pp. 1441-1460, vol. 12, Copernicus Publications on behalf of the European Geosciences Union, 20 pages.

International Search Report and Written Opinion from the US International Search Authority for International Application No. PCT/US2020/012247 dated Mar. 10, 2020, 13 pages.

* cited by examiner

APPARATUS AND METHODS FOR REDUCING FUGITIVE GAS EMISSIONS AT OIL FACILITIES

TECHNICAL FIELD

This disclosure pertains generally, but not by way of limitation, to systems and methods for reducing fugitive emissions. In particular, the system and methods described herein provide remote monitoring of oil facilities that are prone to leaking natural gas.

CROSS REFERENCE TO RELATED APPLICATION

The present application claims priority to (i.e., is a non-provisional of) U.S. Provisional Patent Application No. 62/795,608 entitled "APPARATUS AND METHODS FOR DETECTING AND REPORTING ENVIRONMENTAL CONDITIONS", and filed 23 Jan. 2019 by DAVID L. ARMITAGE. The present application also claims priority to (i.e., is a non-provisional of) U.S. Provisional Patent Application No. 62/851,563 entitled "APPARATUS AND METHODS FOR DETECTING AND REPORTING ENVIRONMENTAL CONDITIONS", and filed 22 May 2019 by DAVID L. ARMITAGE. The entirety of the aforementioned applications are incorporated herein by reference for all purposes.

BACKGROUND

Monitoring and reducing air pollution is critical to our ecosystem. Historically, air monitoring has been an imperfect science including visual diagnostics or other human senses (e.g. hearing, smelling, etc.). Recently, portable and handheld sensors have been utilized to sample air as part of simple air monitoring. These handheld sensors have been utilized to locate emission sources (e.g. methane emission—a chemical compound that is the main constituent of natural gas). Methane is an attractive fuel, however capturing and storing it becomes difficult. Evidence of this difficulty is that atmospheric methane concentration has increased by about 150% since 1750 which is a problem because methane increases total radiative forcing from greenhouse gases (i.e. causing global warming). While monitoring and reducing air pollution is critical, the above human and/or sensor systems have had limitations (e.g. being non-simultaneous, inaccurate, overly-complex, expensive, etc.).

SUMMARY

The detection and reporting of pollution from an oil facility is important for a variety of reasons (e.g. corporate performance, quality of environment, regulatory requirements, etc.). For example, an oil facility removing natural gas (and/or oil) from an underground reservoir utilizes equipment (e.g. pumpjacks, holding tanks, valves, pipes, etc.) that requires maintenance. Occasionally, this equipment releases pollution into the atmosphere. This release into the atmosphere is called 'fugitive gas emission' or generically 'pollution' that should be detected and reported so corrective action may be taken.

To address emission/pollution, the disclosed system monitors, detects, and reports the differential concentrations of gas from a population of monitors located around the perimeter of a site. Differential concentrations of gas from a population (of monitors located in a monitored area) indicates presence of a leak. An oil facility configured with the present system can sense the increase/presence of emissions by comparing readings from a plurality of pollution monitors. Each pollution monitor utilizes a logic control system to read at least one pollution sensor; furthermore, the aggregation of pollution monitors presents the sensed site data to determine if there is a leak. The pollution leak can be addressed accordingly (e.g. noted, repaired, observed, etc.).

One general aspect of a pollution monitor for an oil facility may include a housing having an interior and an exterior provided with a first venturi opening formed in the housing to allow airflow between the exterior and interior. The housing may further include a second venturi opening configured to allow airflow between the interior and exterior with an airstream path in the interior between the first venturi opening and the second venturi opening. The pollution monitor further includes an electronics package positioned in the interior of the housing adjacent to the airstream path. The electronics package may include a pollution sensor electrically interfaced with the electronics package and configured to output a signal representative of an airborne pollutant concentration. The electronics package may further include a communications module electrically interfaced with the electronics package and configured to transmit the airborne pollutant concentration. The pollution monitor may further include a panel mount attached to the housing including a top and a pitch angle formed between the top and a global-horizontal plane. The pitch angle may be greater than zero degrees and have a solar panel attached to the top of the panel mount. The solar panel is electrically interfaced with the electronics package and configured to drain water. The solar panel may be configured to maximize solar charging and have a power conductor electrically interfaced with the solar panel. The power conductor terminates at the electronics package and may pass through the housing. All of these cooperate to provide a system for reducing fugitive gas emissions at an oil facility as described herein.

In another general aspect, a method for sampling air pollution at an oil facility may include a pollution monitor having a housing. The housing may be configured to receive one or more components and to protect the components from outdoor environmental conditions. These optional components may include an electronics package disposed in the housing, and a pollution sensor in electrical communication with the electronics package. The pollution sensor may be configured to output a signal representative of a pollutant concentration. The pollution monitor may further include a location defined by geolocation and a physical sampling system in electrical communication with the electronics package. The method for sampling may further include establishing a rule for invoking a sampling event, and monitoring for breach of the rule. Upon breach of the rule, the pollution monitor may be invoked to initiate sampling of air pollution by capturing a sample of air with the physical sampling system, and storing the location of the sample of air.

In another general aspect, a method for reporting atmospheric pollution originating at an oil facility may include providing a first pollution monitor having a housing configured to receive components of the pollution monitor and to protect the components from environmental conditions. The components may include an electronics package adjacent to the housing. Furthermore, the components may include a first pollution sensor in electrical communication with the electronics package, and the first pollution sensor may be configured to report atmospheric level of a first amount of pollution. The first pollution monitor may include a first location defined by a geographic coordinate. The method may include providing a second pollution monitor including a housing configured to receive components of the second pollution monitor and to protect the components from environmental conditions. The second pollution monitor may include an electronics package adjacent to the housing and a second pollution sensor in electrical communication with the electronics package. The second pollution sensor may be configured to report a second amount of pollution. The second pollution monitor may include a second location defined by a geographic coordinate that is different than the first location. The method may further include comparing the first amount of pollution reported by the first pollution sensor to the second amount of pollution reported by the second pollution sensor. The method may further include reporting atmospheric pollution originating at the oil facility when the first amount of pollution is different than the second amount of pollution. And, the method may create, after the reporting, instructions to address the pollution originating at the oil facility.

BRIEF DESCRIPTION OF THE DRAWINGS

The accompanying figures of the drawing, which are included to provide a further understanding of general aspects of the system/method, are incorporated in and constitute a part of this specification. These illustrative aspects of the system/method, and together with the detailed description, explain the principles of the system. No attempt is made to show structural details in more detail than is necessary for a fundamental understanding of the system and various ways in which it is practiced. The following figures of the drawing include.

In the appended figures, similar components and/or features may have the same numerical reference label. Further, various components of the same type may be distinguished by following the reference label with a letter. If only the first numerical reference label is used in the specification, the description is applicable to any one of the similar components and/or features having the same first numerical reference label irrespective of the suffix.

DETAILED DESCRIPTION

The ensuing description provides preferred illustrative embodiments only, and is not intended to limit the scope, applicability or configuration of the disclosure. Rather, the ensuing description of the preferred illustrative embodiments will provide those skilled in the art with an enabling description for implementing a preferred illustrative embodiment. It is understood that various changes may be made in the function and arrangement of the elements without departing from the spirit and scope set forth in the appended claims. It should be noted that while the following description is configured for an oil and gas facility, other areas that may be configured with the present system. For example, the system may be utilized at locations ranging from rural marshlands to urban industrial facilities. Other examples of monitored areas include, but are not limited to: beaches (for red-tide blooms), gas stations, painting facilities, parking lots, cattle feed lots, rendering facilities, propane refilling stations, truck servicing bays, etc. As used herein, the term 'monitored area' means any location where pollution presence (in or around) is monitored. The monitored site may be relatively large or, in one example configured as a wellsite, relatively small of about 0.2 to 2 acres. One application for the present pollution monitor is at/in/near 'oil facilities' such as: well sites, drilling rigs, service rigs, offshore platforms, refineries, petrochemical plants, gas plants, pipelines, tank farms, wellheads, pump jacks, etc.

Figure 1:
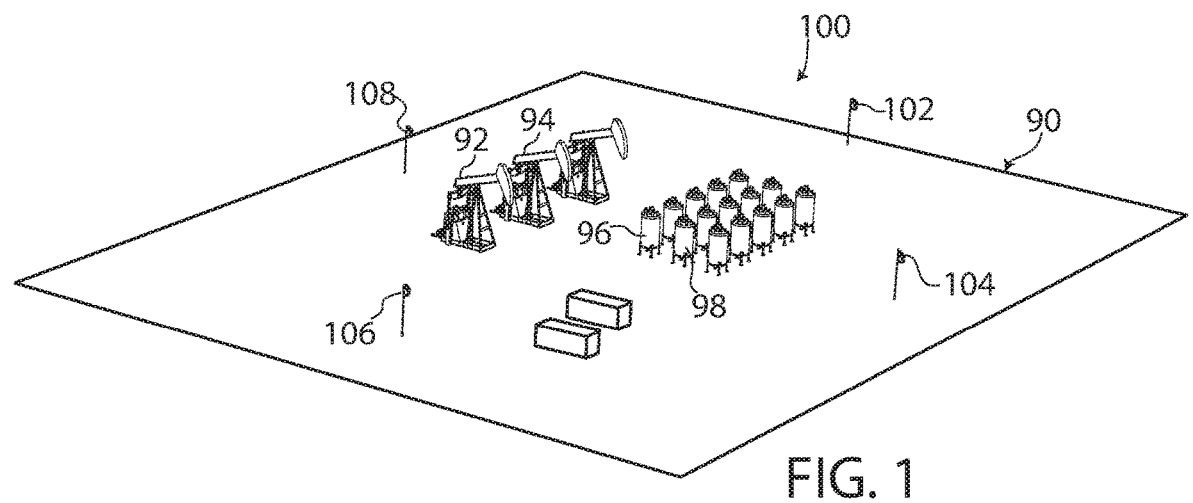
FIG. 1 is a perspective view a monitored area (e.g. an oil facility configured as a wellsite) provided with a plurality of pollution monitors, according to an illustrative embodiment of the present disclosure.

With reference to FIG. 1 showing a monitored area 90 at an oil facility 100, the system for reducing fugitive gas emissions may detect and report pollution at the oil facility 100 with pollution monitors 102, 104, 106 and 108. In general terms, the monitored area 90 may be located in an oil-producing region and oil facility 100 may include various industrial items such as pumpjacks 92, 94 and holding tanks 96, 98. The pumpjacks and holding tanks are in fluid communication with each other by a network of pipes (not shown). Oil and/or gas is pulled from an underground reservoir (not shown) via the pumpjack 92 and distributed to the holding tank 96. Occasionally, constituents of oil/gas (e.g. hydrocarbons such as: methane, ethane, butane, pentane, hexanes, etc., and other fluids in either liquid or gas state, e.g.: nitrogen, carbon dioxide, oxygen, hydrogen, rare gasses, etc.) are discharged into the atmosphere. This discharge into the atmosphere is called fugitive emission and/or pollution that is man-made (anthropogenic). For example, if a packing gland of the pumpjack 92 is expired, hydrocarbons may be discharged (i.e. leak) from the packing gland. The oil facility 100 configured with the present system can sense the increase/presence of emissions by comparing readings from one or more of the pollution monitors 102, 104, 106, 108 as described herein.

Figure 2:
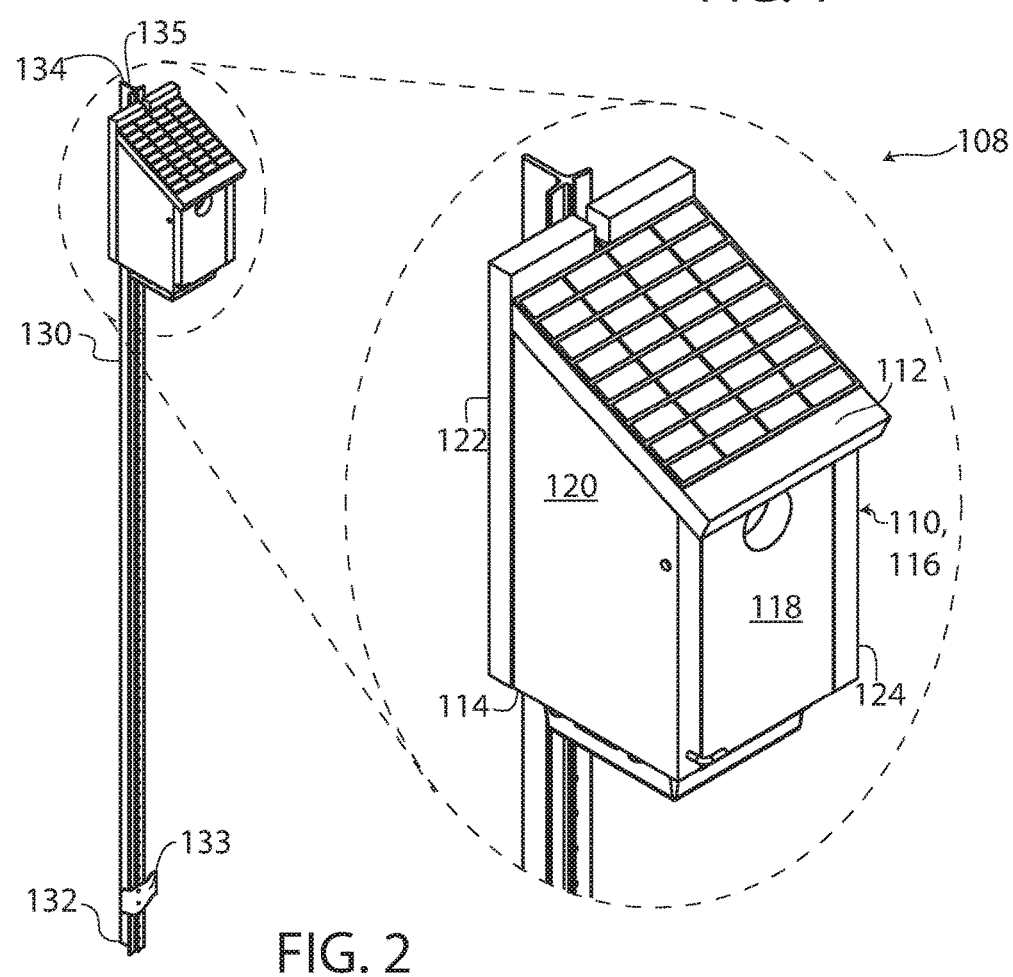
FIG. 2 is a perspective view of an illustrative pollution monitor attached to a vertical object (e.g. a T-post), according to an illustrative embodiment of the present disclosure.

With reference to FIG. 2 showing an illustrative pollution monitor, the pollution monitor 108 may be configured in any variety of forms such as the useful configuration disguised as a birdhouse. The term 'birdhouse' is synonymous with 'bird habitat' and refers to any artificial interior portion capable of receiving and sheltering at least one bird from the elements. Passage from the interior portion to the exterior portion is enabled by a bird passage as described herein. In the illustrated configuration, the pollution monitor 108 may include a 'panel mount' configured as an insulating body 110 having a top 112 and an oppositely disposed bottom 114 separated by a box 116. The box 116 includes perimeter walls referred herein as a front face 118, a left side 120, a back face 122, and a right side 124. The box 116 is a structure that has an interior area 126 (FIG. 5) that is substantially blocked from ambient conditions of an exterior area. In one embodiment, the front face 118, left side 120, back face 122, right side 124, top 112, and bottom 114 are made of wood. However, the insulating body 110 can be made in a large variety of configurations with a variety of materials. As used herein the term 'panel mount' means a structure capable of supporting a solar panel (e.g. the insulating body 110, a fixed bracket, one or more angle brackets, a pivot, etc.).

With continued reference to FIG. 2, the insulating body 110 is capable of shielding heat at the insulating body top 112 from transferring to the insulating body bottom 114 (i.e. blocking heat from transferring through the insulating body 110). As used herein, the term 'insulating body' means a structure designed to block heat transfer from a top surface to a bottom surface. To be clear, while most materials provide some level of insulation, the present configuration of the panel mount includes an insulating body that intentionally blocks heat transfer. While a variety of structures/materials may be deployed to block heat transfer, specific examples include: foamed plastic sheet, spun fibers compressed into a board, natural organic(s) formed into a planar object, wood board, a birdhouse, concrete structure, a ribbed plastic structure with airgaps, etc. While the insulating body 110 may be a variety of thicknesses, one configuration includes a thickness of eight to ten inches. In another configuration, the insulating body 110 may be about an inch thick, or 0.25 inches to two inches, or the thickness may be between two and eight inches depending on the particular configuration. In one specific configuration, the insulating body includes a large interior portion of stagnant air configured to receive a bird which is eight inches at the front face 118 and ten inches at the back face 122.

With continued reference to FIG. 2, the pollution monitor 108 may be attached to any of a variety of 'vertical objects', such as the T-post 130 as illustrated. The T-post 130 is a readily installable and a suitably stationary object to which the pollution monitor 108 may be attached. The T-post 130 may be configured a length of metal (e.g. steel) having a spade end 132 and an oppositely disposed top end 134 as illustrated. The T-post 130 may be configured with a spade 133 located at the spade end 132 and further configured with an anvil 135 located at the top end 134. The T-post spade end 132 is anchored (by manual or machine impact) into ground at the monitored area 90 such that the T-post top end 134 is about, for example, 5 feet in the air. This orientation allows the top end 134 of the T-post 130 to be clear from objects such as grass, bushes, trees, buildings, snow, standing water, small animals, etc. Therefore, any reasonably elongated member of the T-post 130 (e.g. over 2 feet) may be enough to keep the pollution monitor 108 above other objects where the intended functionality can be performed. The T-post 130 (sometimes referred to herein as a 'vertical object') may be made of a material with a geometry that can support the pollution monitor 108. The cross-sectional view of the T-post may, in one example, be a 'T' that is easily driven into the ground with a manual or pneumatic post pounder. The T-post 130 may be provided with studs (FIG. 10) that prevent attached components (e.g. the pollution monitor 108 and the spade 133) from sliding down the T-post 130.

With continued reference to FIG. 2, the pollution monitor 108 may be attached to the top end 134 of the T-post 130 by any of any one of a variety of mechanical means such as a U-bolt 138 (FIG. 3), alternatives include, but are not limited to: band clamps, wire ties, bolts, rivets, screws, adhesive, etc. Additionally, the process of installing other pollution monitors (e.g. 104, 106, 108 shown in FIG. 1) may be the same as installing pollution monitor 108 in the monitored area 90. If powered by a solar panel (described herein), the front face 118 may generally face south when installed in North America.

Figure 3:
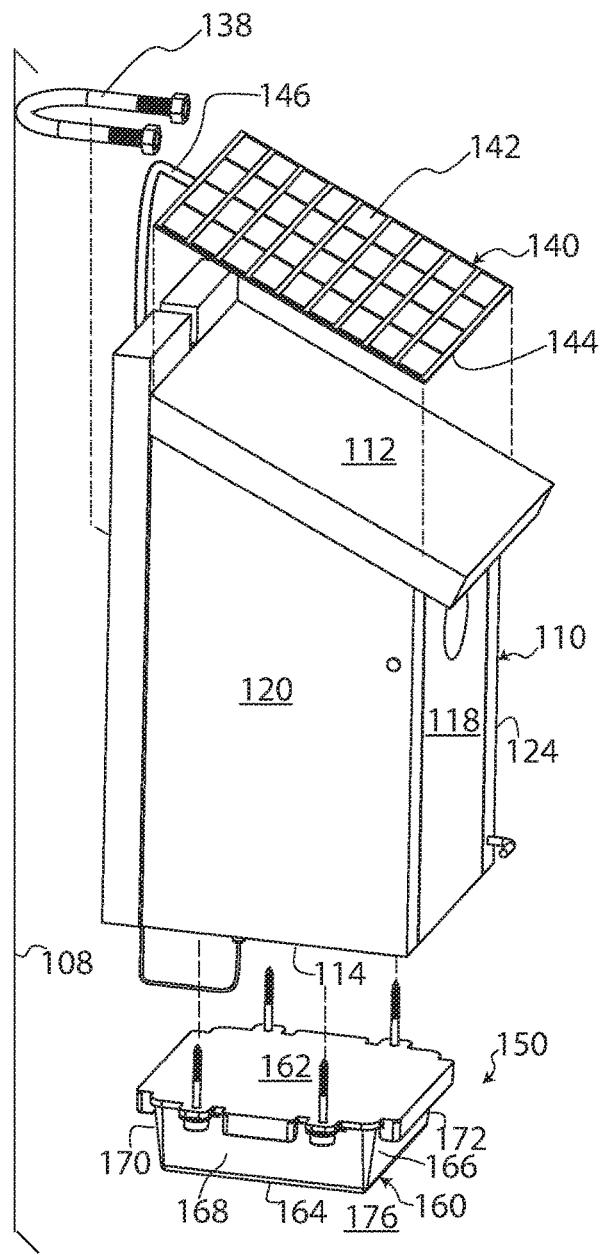
FIG. 3 is a perspective view of an illustrative pollution monitor in an exploded condition, according to an illustrative embodiment of the present disclosure.
Figure 4:
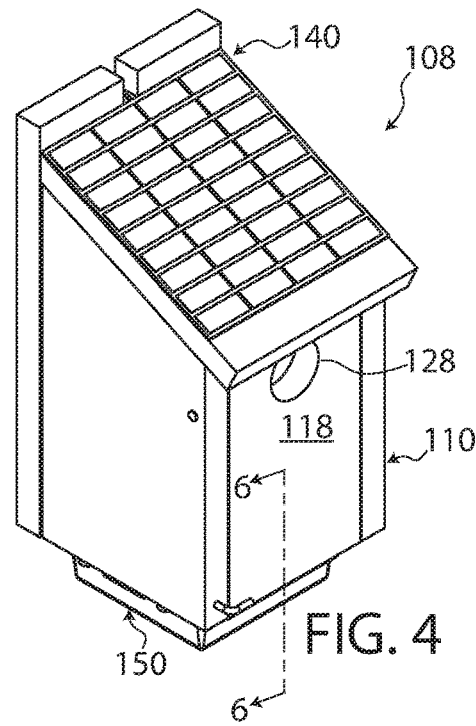
FIG. 4 is a perspective view of the pollution monitor of FIG. 3 in an assembled condition.
Figure 40:
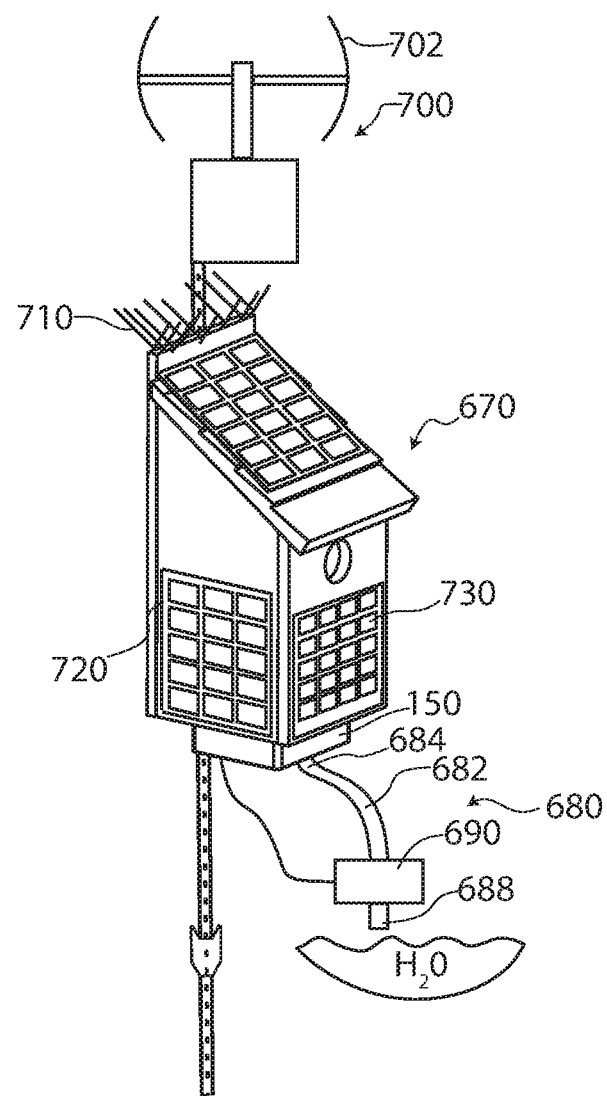
FIG. 40 is a perspective view of an illustrative pollution monitor configured with an optional meteorological system (e.g. a wind sensor), an optional air conveyance tube, an optional bird deterrent mechanism, and optional booster solar panels, according to illustrative embodiments of the present disclosure.
Figure 41:
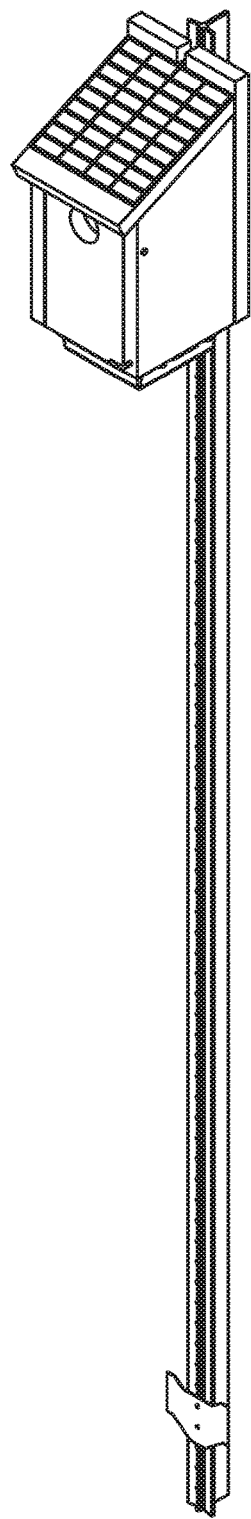
FIG. 41 is a perspective view of an illustrative pollution monitor configured with a vertical object, according to an illustrative embodiment of the present disclosure.
Figure 42:
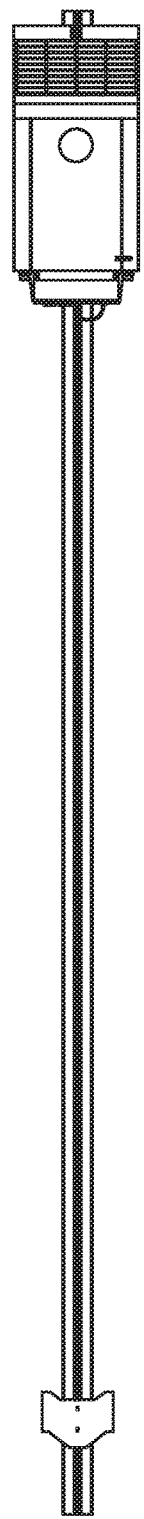
FIG. 42 is a front elevation view of the pollution monitor of FIG. 41.
Figure 43:
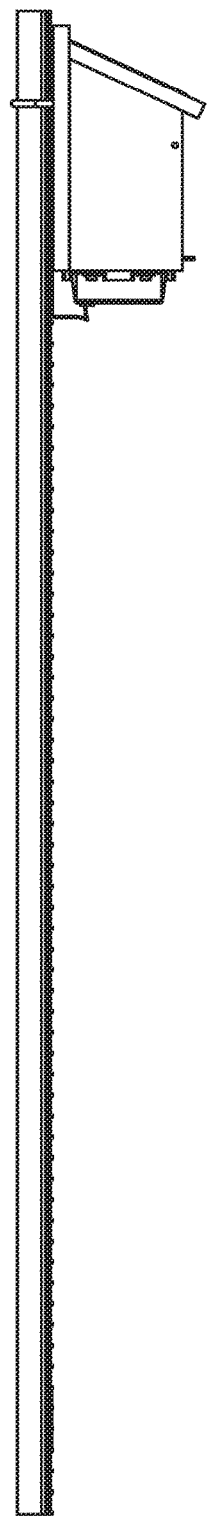
FIG. 43 is a left side elevation view of the pollution monitor of FIG. 41.
Figure 44:
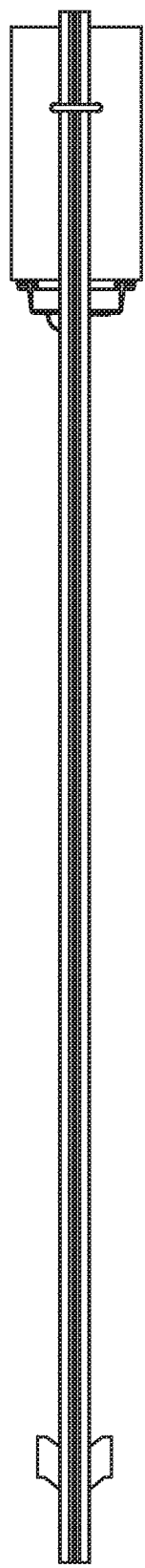
FIG. 44 is a back elevation view of the pollution monitor of FIG. 41.
Figure 45:
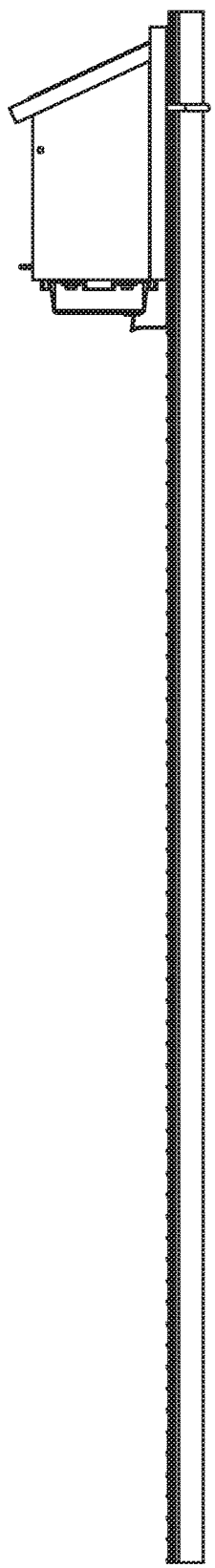
FIG. 45 is a right side elevation view of the pollution monitor of FIG. 41.
Figure 46:
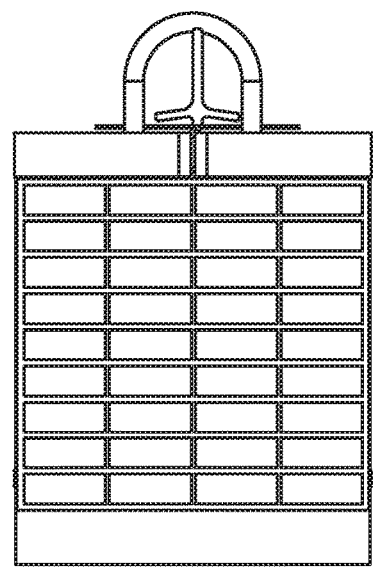
FIG. 46 is a top plan view of the pollution monitor of FIG. 41.
Figure 47:
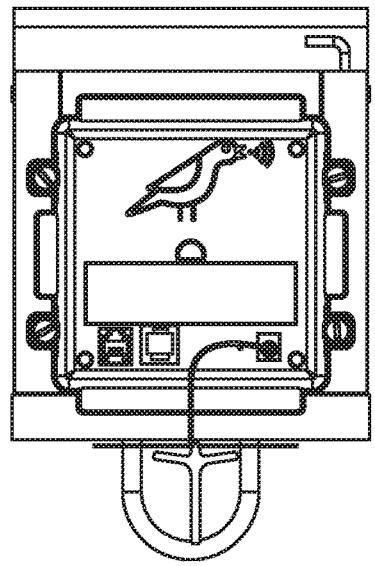
FIG. 47 is a bottom plan view of the pollution monitor of FIG. 41.
Figure 48:
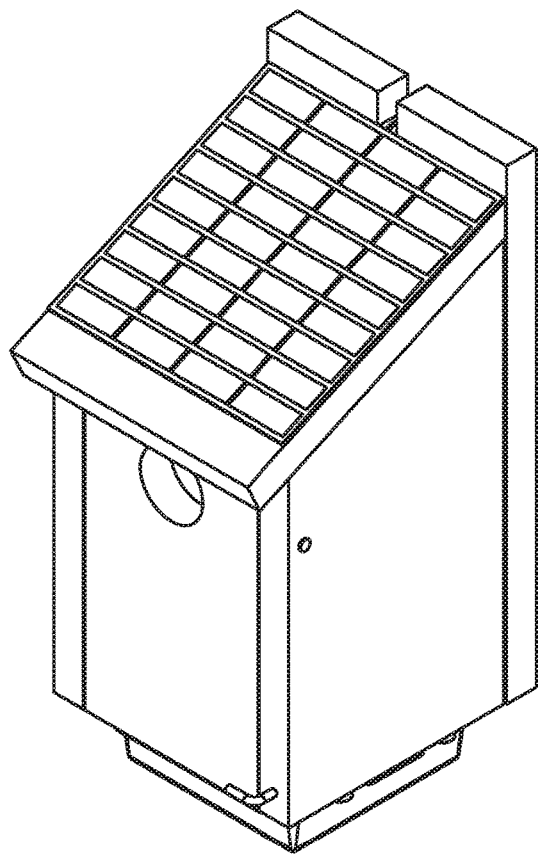
FIG. 48 is a perspective view of a pollution monitor, according to an illustrative embodiment of the present disclosure.
Figure 49:
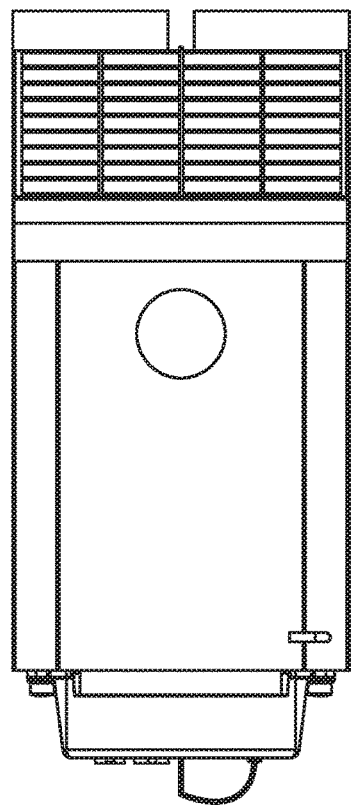
FIG. 49 is a front elevation view of the pollution monitor of FIG. 48.
Figure 50:
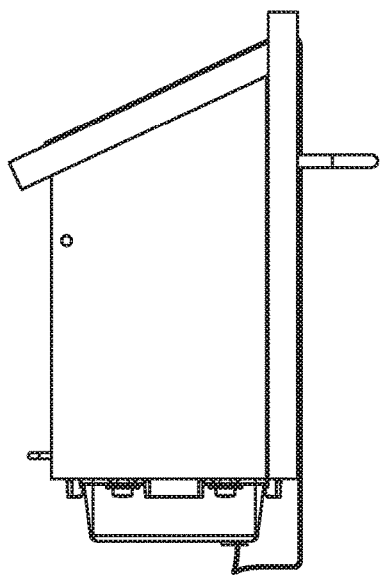
FIG. 50 is a left side elevation view of the pollution monitor of FIG. 48.
Figure 51:
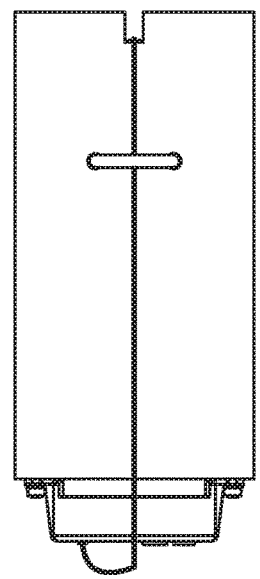
FIG. 51 is a back elevation view of the pollution monitor of FIG. 48.
Figure 52:
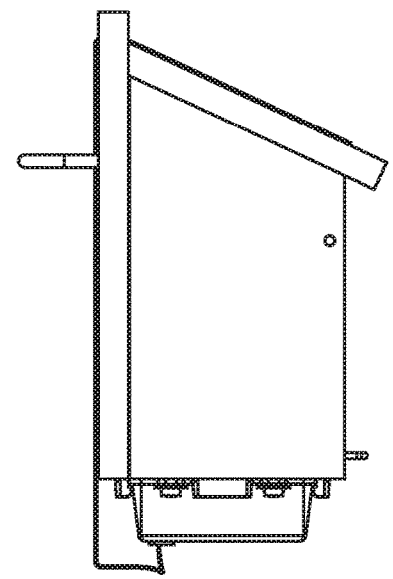
FIG. 52 is a right side elevation view of the pollution monitor of FIG. 48.
Figure 53:
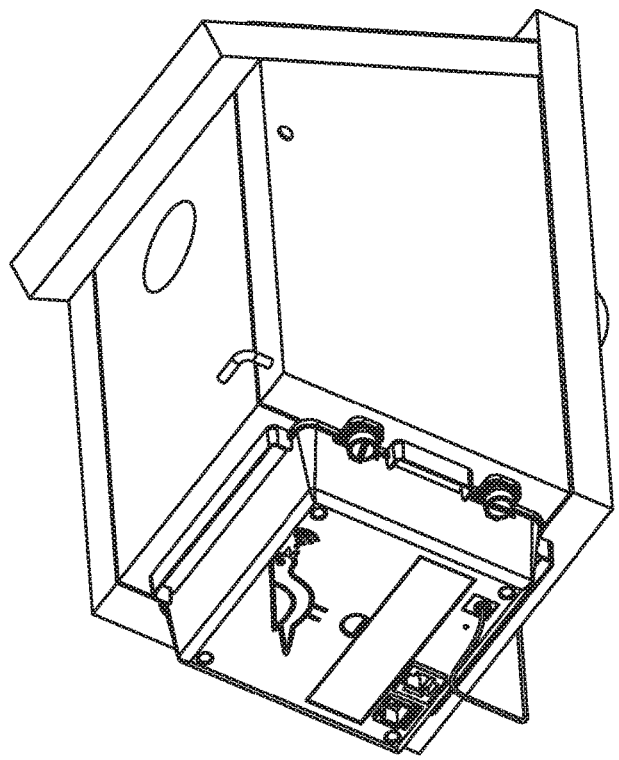
FIG. 53 is a bottom side perspective view of the pollution monitor of FIG. 48.
Figure 54:
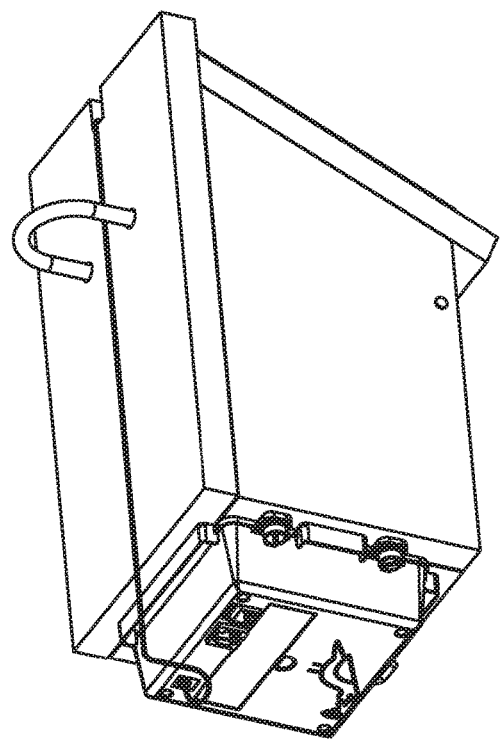
FIG. 54 is another bottom side perspective view of the pollution monitor of FIG. 48.
Figure 55:
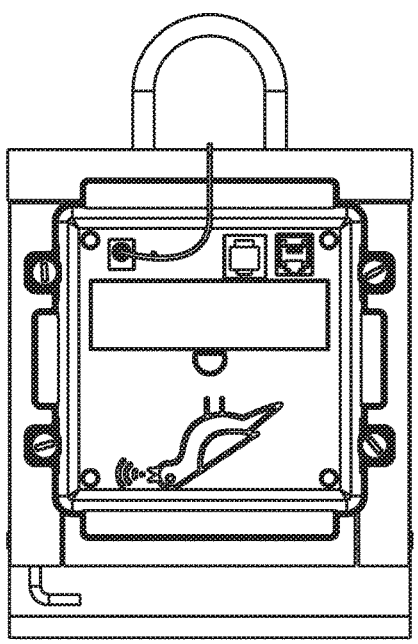
FIG. 55 is a bottom plan view of the pollution monitor of FIG. 48.
Figure 56:
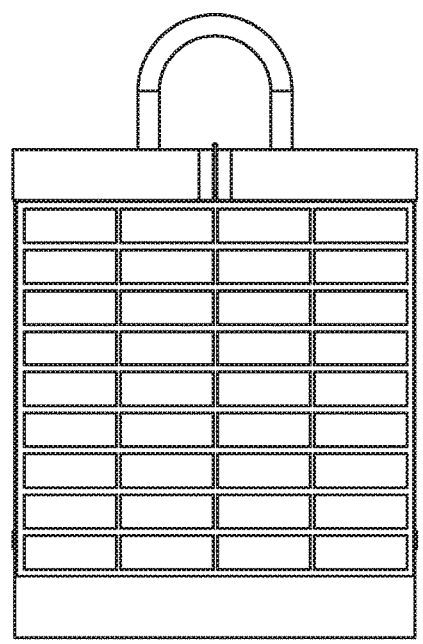
FIG. 56 is a top plan view of the pollution monitor of FIG. 48.

With reference to FIG. 3 illustrating a perspective view of the pollution monitor 108 in an exploded condition without the vertical object (T-post 130), the pollution monitor 108 is provided with a power system (e.g. a permanent battery, a rechargeable battery, a thermo-electric system, a hydro-electric system, etc.) such as a solar panel 140. The solar panel 140 is a generally planar object capable of converting energy from the sun into electrons through a photovoltaic process. The solar panel 140 includes a top surface 142, an opposite bottom surface 144, and a power lead 146. The solar panel top surface 142 may include silicon wafers generating electrons that flow to the bottom surface 144 and continue to an electronics package 150 via the power lead 146. The solar panel bottom surface 144 may be attached to the panel mount (e.g. configured as the insulating body top 112) by any of a variety of attachment methods, such as with a pivot bracket (not shown), mechanical fasteners (not shown), or adhesive as illustrated (FIG. 4). The solar panel 140 may be constructed of traditional or specialized components. Traditional methods of construction include epoxy encapsulation while more specialized construction includes ethel vinyl acetate (EVA) encapsulation with an ETFE sheet protection at the outermost surface. In one example, the solar panel 140 is configured with a number of individual solar cells that are configured to match the solar panel's maximum power point to the average charge voltage of the battery. The solar panel 140 may be separated from the insulating body 110, or it may be provided as a number of individual panels such as individual panels attached to the front face 118, the left side 120, and/or the right side 124 (FIG. 40).

With continued reference to FIG. 3, the electronics package 150 may include a housing 160. The electronics package housing 160 may be made of any structural material (such as metal, wood, or plastic) and generally defines a top 162 and an oppositely disposed bottom 164. The housing top 162 and bottom 164 are separated by a perimeter of walls, specifically a front wall 166, a left wall 168, a back wall 170, and a right wall 172. The electronic assembly 150 may be attached to the bottom 114 of the insulating body 110 via any of a variety of methods such as mechanical fasteners (e.g. screws as shown) thereby creating an internal portion 174 (FIG. 6) and an exterior portion 176 (the exterior portion 176 is at ambient condition).

Figure 5:
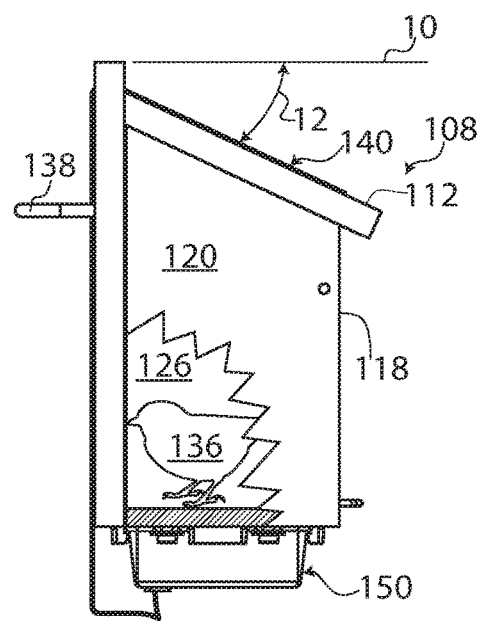
FIG. 5 is a side elevation view of an illustrative pollution monitor wherein an insulating body is configured as a bird habitat, according to an illustrative embodiment of the present disclosure.

With reference to FIG. 4 illustrating a perspective view of the pollution monitor 108 with the solar panel 140 and electronics package 150 attached thereto, the pollution monitor may be configured as a bird habitat where the insulating body 110 includes a bird passage 128 formed in the insulating body front face 118. The bird passage 128 provides a pathway for a bird 136 (FIG. 5) to move from ambient conditions at the exterior portion 176 into the interior area 126 as illustrated in FIG. 5. In this illustrative configuration, the pollution monitor 108 is configured as a birdhouse so that it blends, aesthetically, into the surroundings and to be a resource to benefit the environment. This illustrated birdhouse configuration (where in the insulating body 110 is shaped as a traditional birdhouse and configured to receive the bird 136), is useful for blocking the high heat (temperature) at the top 112 from the electronics package 150. The insulating body 110 may take other forms ranging from a simple piece of insulating material (e.g. a low-conduction material, a plate of structural foam, a hollow box, etc.) to a more elaborate configuration as can be appreciated by one skilled in the art with the benefits and teachings of the present document. In one example, the insulating body 110 and the housing 160 may be combined in a simple enclosure such as a 'project box' used for housing electronics. In this project box configuration, the solar panel 140 is simply attached to one face of the box or may be held by a panel mount (either fixed or adjustable).

With reference to FIG. 5 showing a side elevation view of the pollution monitor 108, (wherein a portion of the insulating body left side 120 has been removed) the bird 136 may take shelter in the interior area 126. Some species of birds have at least a partially insectivorous diet and insects are a source of protein for nestlings. Examples of insectivorous birds include bluebirds, dippers, flycatchers, swallows, and wrens. It may be useful to include a birdhouse with the pollution monitor 108 to avoid insects from seeking refuge in the pollution monitor 108 (either in the insulating body 110 or the housing 160 of the electronics package 150).

With continued reference to FIG. 5, the pollution monitor 108 may be configured such that the top 112 is able to shed rain (i.e. drain water) and positioned for maximum solar-charging, and therefore angled relative to a global-horizontal plane 10. This global-horizontal plane 10 is useful while describing features of the environmental monitoring 108. As used herein, the term 'global-horizontal plane' is a plane with a point that is colinear to local gravity direction and intersects perpendicular to the global-horizontal plane 10 (also referred to as 'level' as defined by a carpentry level). Therefore, the top 112 of the insulating body 110 resides in a plane that intersects the global-horizontal plane 10 at an angle of intersection referred to herein as a pitch angle 12. The pitch angle 12 may be any non-zero angle, such as 45 degrees which is ideal for optimally positioning the solar panel 140 relative to the sun facing south in North American installations. The pitch angle 12 for North America is 35 degrees plus or minus 20 degrees, that results in the top 112 positioned normal to the sun at solar-noon on winter solstice (11:58 am on 21 Dec. 2019 in Denver, Colo.). The power lead 146 serves as part of a power conductor to move power from the solar panel 140 to the electronics package 150 via the solar connection 252 (described herein). Therefore, the power conductor configured as power lead 146 and solar connection 252 pass 'through' the housing 160 to deliver power from the solar panel 140 to the battery.

Figure 6:
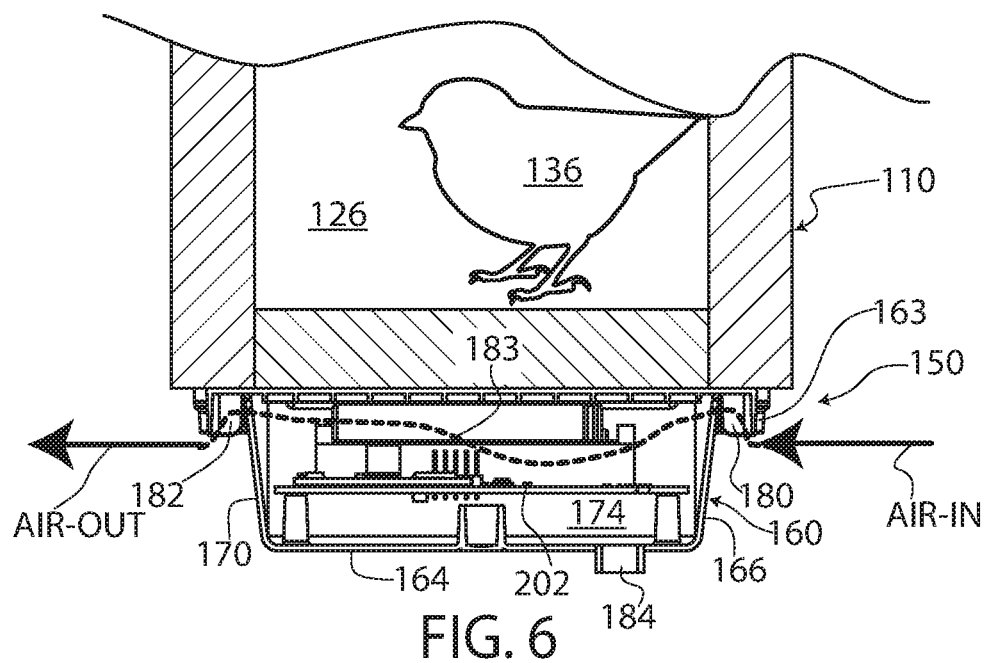
FIG. 6 is a cross-section side elevation view of the pollution monitor of FIG. 4 taken across plane 6-6.

With reference to FIG. 6 illustrating a side view of the pollution monitor 108 taken across plane 6-6 (FIG. 4), the electronics package housing 160 may include features causing ambient air to flow into (and subsequently out of) the internal portion 174. A simple but energy-consuming configuration is an air pump, but other configurations have proven useful. If provided with features for causing airflow, the housing 160 may include several venturi openings such as a first venturi opening 180 and a second venturi opening 182. While any number of venturi openings may be provided in any surface of the package housing 160, the first venturi opening 180 may be formed in the housing front wall 166 near the top 162 (FIG. 3). In a similar manner, the second venturi opening 182 may be formed in the housing back wall 170 near the top 162. When the electronics package 150 is attached to the insulating body 110, the first venturi opening 180 and second venturi opening 182 form openings through which moving air can travel along an airstream path 183 (located in the internal portion 174 as illustrated). Moving air causes a pressure drop inside the electronics package 150 which is utilized to move air into and mixed inside the electronics package internal portion 174. In one illustrative embodiment, the electronics package 150 may further include a sensor opening 184 formed in the bottom 164 of the housing 160. As air moves from the first venturi opening 180 through the internal portion 174, it moves ambient air across at least one sensor for a purpose described herein. The air ultimately escapes the housing 160 through the second venturi opening 182 (or other openings).

With continued reference to FIG. 6, the venturi openings 180, 182 cooperate to move air and draw ambient air across a pollution sensor 202. The dark flow lines in FIG. 6 illustrate the flow of air through the electronics package 150. In addition to the pollution sensor 202, other sensors may be placed in the flow of air for the purposes of expansive measurements and/or providing redundancy. For example, other sensors that may be substituted, augmented, placed in multiples, include but are not limited to sensors that detect fluids (e.g. methane, ethane, propane, butane, carbon dioxide, oxygen, nitrogen, hydrogen sulfide, rare gasses, etc.).

Figure 7:
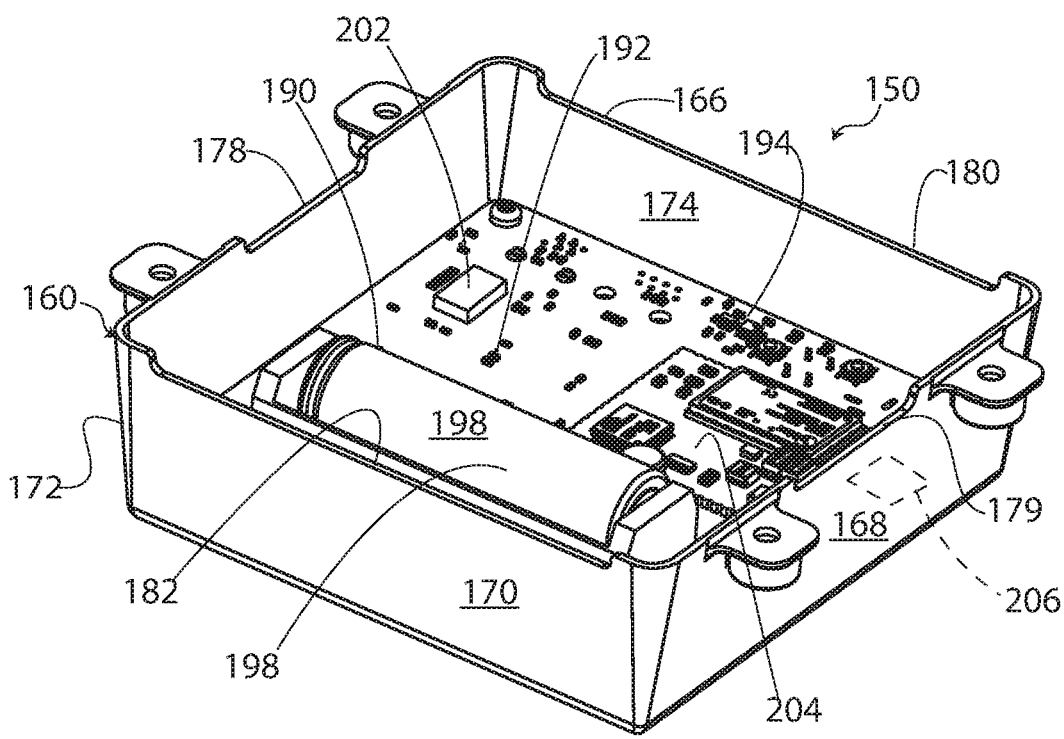
FIG. 7 is a perspective view of an electronics package of an illustrative pollution monitor wherein a top is remove for illustrative purposes, according to an illustrative embodiment of the present disclosure.

With reference to FIG. 7 illustrating a perspective view of an illustrative electronics package 150, the electronics package 150 may be provided with a logic control system 190, a watchdog system 192, a power management module 194, a power supply (e.g. the solar panel 140, FIG. 3), a battery 198, a meteorological module 200, at least one pollution sensor 202, a communications module 204, and a global positioning sensor 206. These various electronics interact to provide the pollution monitoring functionality at the monitored oil facility.

With continued reference to FIG. 7, at the heart of the electronics package 150 is the logic control system 190 that performs operational instructions. The watchdog system 192, if provided, is an electronic timer used to detect and recover from malfunctions of the logic control system 190. During normal operation, the logic control system 190 may regularly reset the watchdog timer 192 to prevent it from elapsing, or 'timing out.' The power management module 194 can be any of a variety of management systems to provide power to the electronics package 150. In the embodiment illustrated, the power management module 194 manages performance and reports quality and status of the power generated by the solar panel 140 (FIG. 4) and subsequently provided to the battery 198. The meteorological module 200, if provided, includes one or more sensors for monitoring environment (e.g. wind speed, direction, temperature, humidity, atmospheric pressure, rainfall, lighting, etc.). The meteorological module 200 may be interfaced with the logic control system 190 via connected or wireless devices (not shown) that provide serial line communication or other protocols utilized by those skilled in the art.

With continued reference to FIG. 7, the pollution sensor 202 may be interfaced with the logic control system 190 via serial line communication or other protocol. While some varieties of the pollution sensor 202 may be mounted outside the electronics package 150, one particular type of sensor may be mounted in the internal portion 174 of the electronics package 150. As best illustrated in FIG. 7, a pollution sensor 202 may be a hydrocarbon sensor capable of measuring a few parts per million (PPM) of hydrocarbons (specifically volatile organic compounds). This hydrocarbon sensor version of the pollution sensor 202 may be at a low temperature and dry location where ambient air is exposed to the pollution sensor 202. The pollution sensor 202 may detect trace amounts of pollution. As used herein, the terms pollution and pollutant are any substance introduced into the environment with undesired effects, or adversely affects the usefulness of a resource. A pollutant causes long- or short-term damage by changing the growth rate of plant or animal species, or by interfering with human amenities, comfort, health, or property values.

As used herein, the term 'pollution sensor' refers to air pollution devices that detect and monitor the presence of air pollution in the surrounding area. There are various types of air pollution sensors such as particulate matter (PM) sensors and gas phase (GP) sensors. The sensor receives an airflow which passes over at least one electrochemical cell that responds to pollutants. To isolate one pollutant or the other, a separate measurement is needed in field tests. Gas-sensitive semiconductor gas sensors (sometimes referred to as heated metal oxide semiconductor, HMOS) are based on the property that certain metal oxides exhibit a change in electrical resistance in the presence of a target gas. This resistance change is caused by a loss or gain of surface oxygen species via reaction with the target gas. There is a well-defined relationship between gas concentration and change in electrical resistance which leads to a measurement of the target gas concentration.

With continued reference to FIG. 7, the communications module 204 may be provided for sending and/or receiving data between a communications infrastructure (e.g. wired, satellite, cellular, long range radio, shortwave radio, Wi-Fi, mesh, or other variants of communication currently utilized in industry or later introduced). The global positioning sensor 206, if provided, may be used for obtaining and reporting location of the pollution monitor 108. In one configuration, the global positioning sensor 206 utilizes satellites to determine its location and may report the installation location of the pollution monitor 108 within a few meters, so deployment of system at the oil facility 100 is relatively quick and the global positioning sensor 206 and logic control system 190 cooperate to send the location via the communications module 204.

Figure 8:
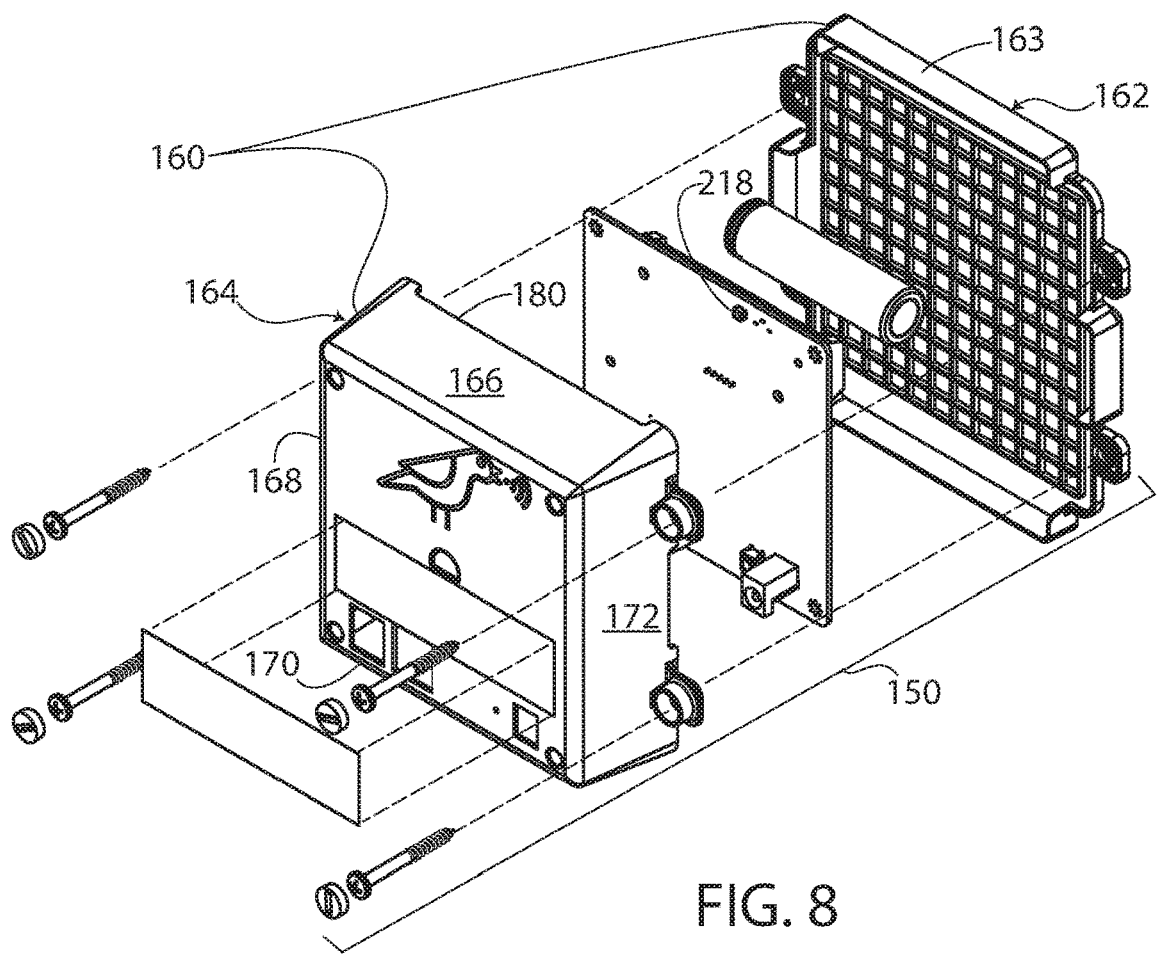
FIG. 8 is a perspective view of the electronics package of FIG. 7 in an exploded condition.
Figure 9:
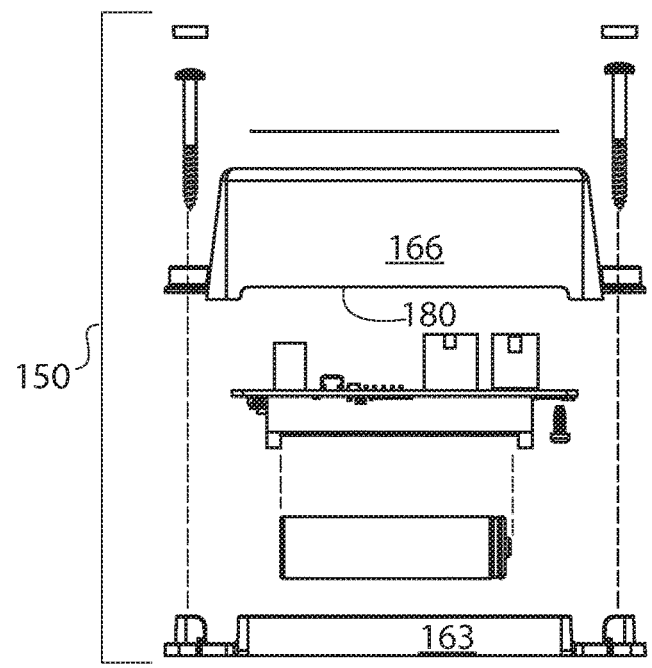
FIG. 9 is a side elevation view of the electronics package of FIG. 7 in an exploded condition.

With reference to FIG. 8 illustrating a perspective view of the electronics package 150 in an exploded condition, the housing 160 may be configured into two pieces retaining their original references as top 162 and bottom 164. The bottom 164 may be configured with the first venturi opening 180 and the second venturi opening 182 formed into the front wall 166 and back wall 170, respectively. Additional openings (e.g. 178, 179, FIG. 7) may be formed into the housing 160 as illustrated. The top 162 may be configured with protrusions formed therein to extend over the openings, such as a brim 163 formed on the top 162 adjacent to the first venturi opening 180. The brim 163 may substantially block horizontally-moving water and debris from entering the internal portion 174. Furthermore, the brim 163 may be (essentially) parallel to the first venturi opening 180 and the front wall 166 (in which the first venturi opening 180 is formed). It is important to note that the use of the term 'parallel' means essentially parallel and not to a high degree of parallelism because manufacturing limitations cause draft angles. This configuration may establish an airgap that is in fluid communication with the internal portion 174 and the exterior portion 176 of the housing 160. Similar protrusions (e.g. brims) may be formed into the top 162 as illustrated for protecting the openings (e.g. 180, 178, 179) from water and debris from entering the internal portion 174.

As illustrated in FIGS. 8-14, the electronics package 150 may be configured to interface with the panel mount configured as the insulating body 110 (FIG. 2) and electrically connected (i.e. electrically coupled, or simply plugged in) to the solar panel 140 (FIG. 2). Alternatively, in one configuration, the pollution monitor may be temporarily deployed wherein the battery 198 (FIG. 7) provides enough power for the temporary deployment. If the deployment is temporary, the electronics package 150 may be relatively small without a solar panel and it may be camouflaged for discrete deployment.

Figure 15:
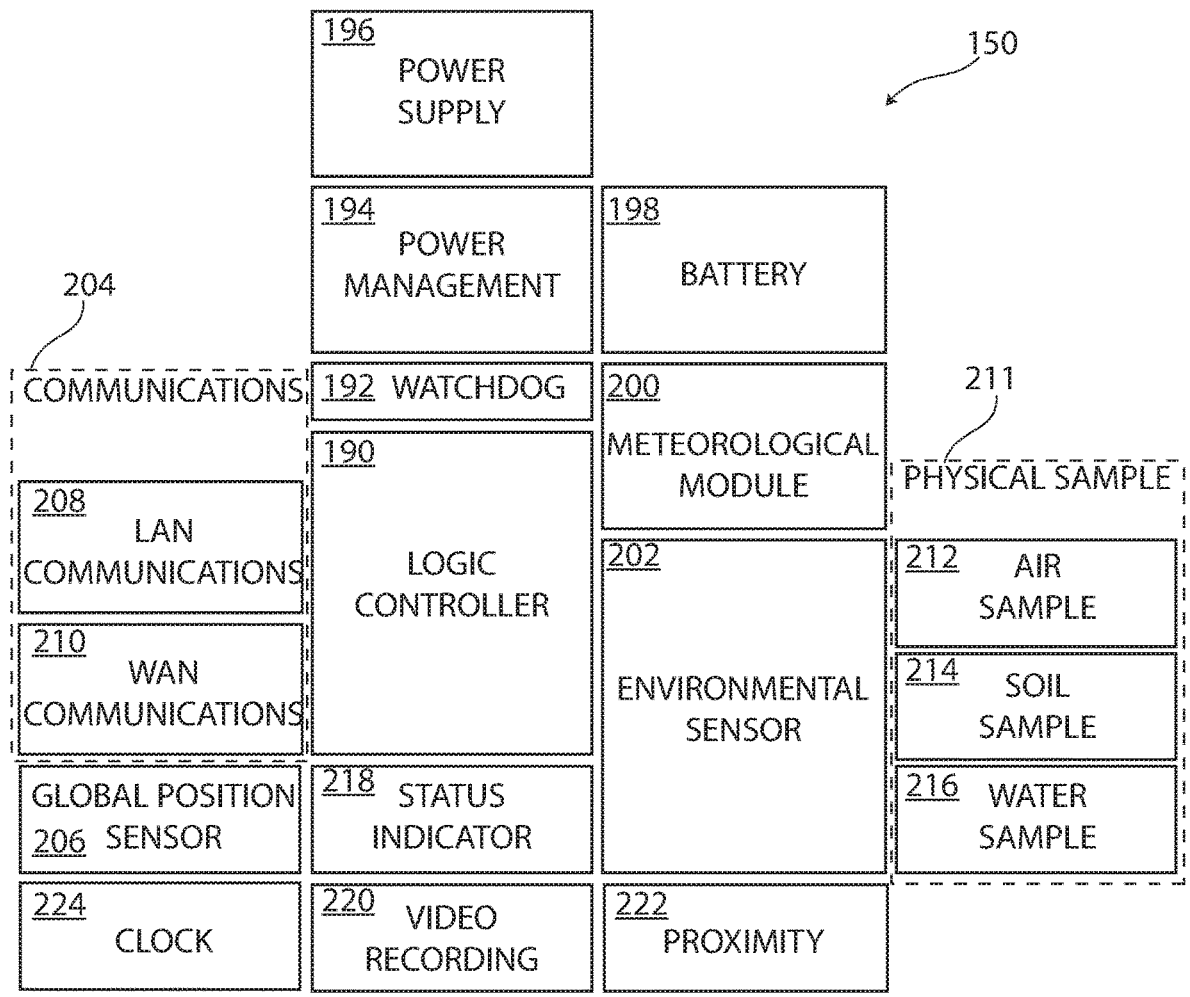
FIG. 15 is a functional schematic of illustrating components of a pollution monitor, according to an illustrative embodiment of the present disclosure.

With reference to FIG. 15 illustrating a functional schematic of various components of an illustrative pollution monitor 108, general communications of the electronics package 150 may be performed by the communications module 204 (e.g. on separate modules such as a LAN communications module 208 and/or a WAN communications module 210). As described herein, the pollution sensor 202 may be verified by separate a physical sampling device (s) 211 such as an air quality sampling module 212, a soil sampling module 214, and/or a groundwater sampling module 216. If required for an application, additional modules may be provided with the electronics package 150 including, for example: a status indicator 218 (also shown in FIG. 10), a video recording module 220 (FIG. 11), a proximity-orientation-movement module 222 (FIG. 11), and/or a clock module 224. One example of the air quality sampling module 212 is described later herein and shown in FIG. 37. Additionally, an example of the groundwater sampling module 216 is described later herein and shown in FIG. 40. The status indicator 218 may or may not be present on the pollution monitor 108—for example, the status indicator 218 (also shown in FIG. 10) may be at least one LED that lights up on the housing 160 or it may be wirelessly transferred to a remote device (e.g. a smartphone or hand-held electronics device, for example). The video recording module 220, if provided, may record in the visible spectrum or may be operating in a non-visible spectrum such as infrared. The proximity-orientation-movement module 222 may be capable of reporting movement of orientation or location indicating that events such as tampering or accidental falling—these events may be usually reported to a remote location via the communications module 204. The clock module 224 can acquire current time and tracking time passage—the clock module 224 generally obtains its set-time via the global positioning sensor 206, the meteorological module 200, the communications module 204 (either LAN communications module 208 or WAN communications module 210) or from other remote system such as the NIST atomic clock and its network-connected services. Other examples include network provided time stamps (e.g. cellular tower), internet services (e.g. cloud server), etc. The time tracked by the clock module 224 may be periodically checked by the logic control system 190 during, for example, a wakeup routine or periodically (e.g. every 12-hours). In each of the individual pollution monitors 102, 104, 106, and 108, the times are synchronized in order to carefully track events. At least one of the individual components of the electronics package 150 has a unique identifier number such as, for example, the EMEI or MAC address of the communications module 204 or a serial number for the logic control system 190. The various modules cooperate to enable various functions of the pollution monitor 108.

FIGS. 16-19 illustrate one configuration of the electronics package 150 provided with a printed circuit board assembly 230. The printed circuit board assembly 230 includes a circuit board 240 having a front side 242 and a back side 244. The printed circuit board assembly 230 may further include: a USB connection 250, a solar connection 252, an analog switch 254, a primary battery holder 256, a secondary battery connector 258, a temperature/humidity sensor 260, a microphone 262, a metrological connector 264, a first pollution sensor 266 (configured as a methane sensor), a second pollution sensor 268 (configured as a primary Volitile Organic Compound, VoC, sensor), a third pollution sensor 270 (configured as a secondary VoC sensor), a physical sample connector 272, a location module 274, a location antenna connector 276, a communications module 278, a communications antenna connector 280, a first expansion connector 282, a second expansion connector 284, a third expansion connector 286, a fourth pollution sensor 288 (configured as a particulate sensor), a boost converter 290, a power switch 292, a voltage regulator 294, a signal translator 296, and other miscellaneous components required for full and optimal operation (e.g. resistors, capacitors, diodes, inductors, light emitting diodes, headers, jumpers, connectors, switches, etc.).

Figure 16:
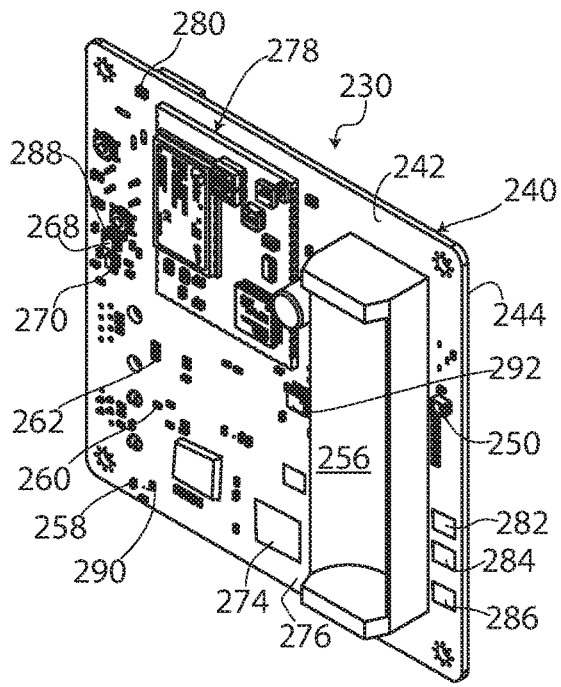
FIG. 16 is a perspective view of illustrative components of an electronics package of the pollution monitor, according to an illustrative embodiment of the present disclosure.

With reference to FIG. 16 showing a perspective view of the printed circuit board assembly 230, the front side 242 of the circuit board 240 may be populated with some of the components. In one illustrative example, the circuit board front side 242 may include the communications module 278 and the communications antenna connector 280 provided for communicating with other pollution monitors, electronic devices, communications towers, satellites, or their equivalents. The illustrative example may include the primary battery holder 256 and the secondary battery connector 258 for receiving either primary or secondary batteries for powering the pollution monitor 108, in one example, the primary battery holder 256 receives an 18650 lithium ion secondary (rechargeable) battery 198 (FIG. 7). The USB connection 250 may be provided for reprogramming or generally to interface other devices during manufacturing and/or servicing. The first expansion connector 282, second expansion connector 284, and third expansion connector 286 may be provided for future feature deployment. The location module 274 and location antenna connector 276 may be supplied for determining location the pollution monitor 108. The first pollution sensor 266, second pollution sensor 268, third pollution sensor 270, and fourth pollution sensor 288 are illustrative examples of a comprehensive approach to determining pollution levels in the local atmosphere of the pollution monitor as described in detail herein. The boost converter 290 may be provided to accurately supply a specific voltage to one or more of the pollution sensors in a process for improving response time and/or accuracy of readings made by the pollution sensors. The temperature/humidity sensor 260 may be provided for evaluating and reporting micro-climate of the internal portion 174 of the electronics package 150.

Figure 17:
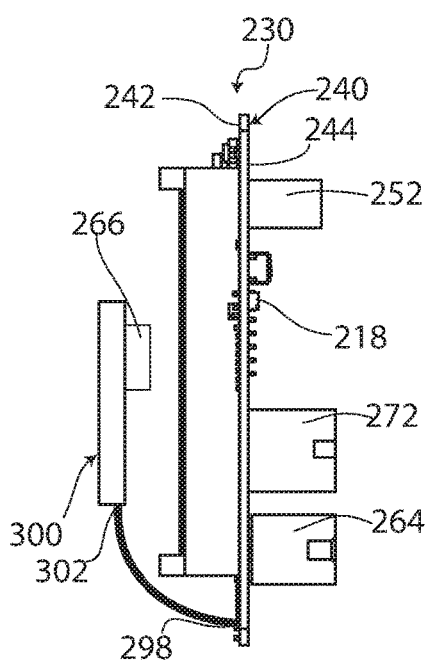
FIG. 17 is a side elevation view of the electronics package of FIG. 16.

With reference to FIG. 17 illustrating a side elevation view of the printed circuit board assembly 230, the back side 244 of the circuit board 240 may be populated with the solar connection 252, the status indicator 218, the physical sample connector 272, and the metrological connector 264. The front side 242 of the circuit board 240 may be configured with a daughterboard connector 298 for receiving a sensor assembly 300. The sensor assembly 300 may include a circuit board 302 and a pollution sensor (e.g. first pollution sensor 266). When configured as shown in FIG. 17, the first pollution sensor 266 and other pollution sensors (e.g. second pollution sensor 268, third pollution sensor 270, fourth pollution sensor 288) may be configured to be in the flow of air through the housing 160 of the electronics package 150 (FIG. 6) whereby the airstream path 183 (FIG. 6) moves the atmospheric air across the pollution sensors.

Figure 18:
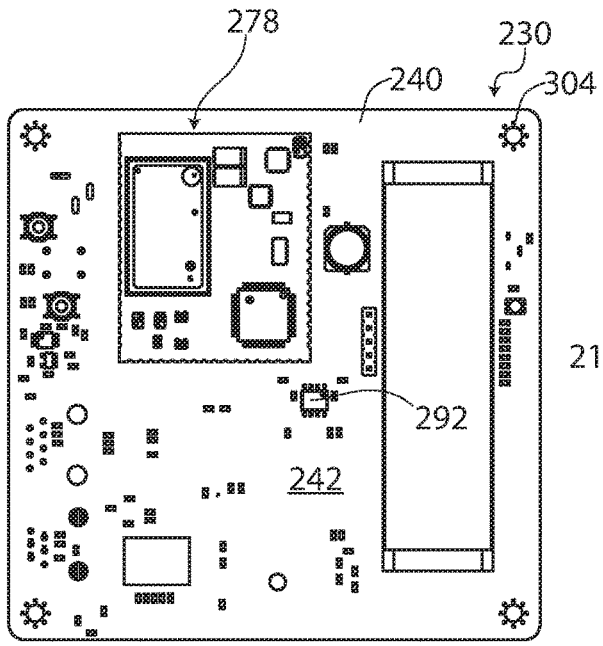
FIG. 18 is a top plan view of the electronics package of FIG. 16.

With reference to FIG. 18 illustrating a top plan view of the printed circuit board assembly 230, the printed circuit board assembly 230 may be configured as illustrated where the communications module 278 is an assembly attached to and in electrical communication with the circuit board 240. The printed circuit board assembly 230 may be provided with a plurality of mounting holes (e.g. mounting hole 304) for attaching it to the housing 160.

Figure 10:
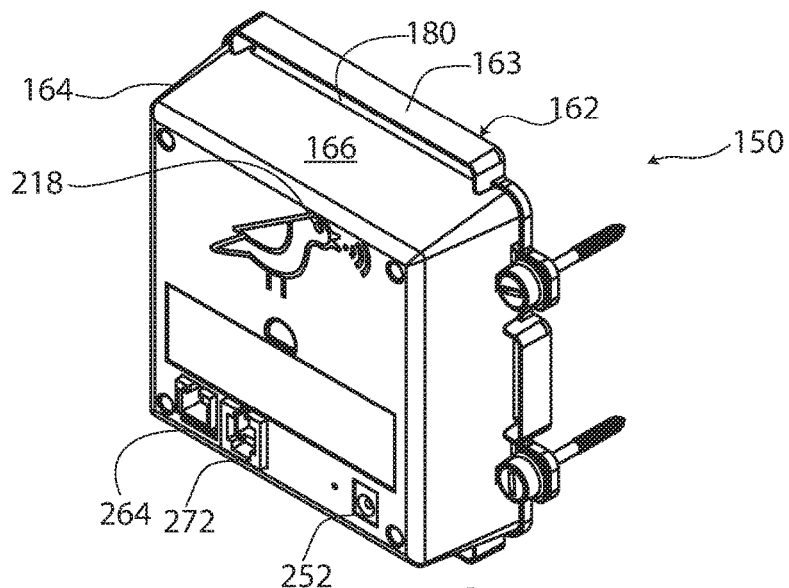
FIG. 10 is a perspective view of the electronics package of FIG. 7 in an assembled condition including a top.
Figure 11:
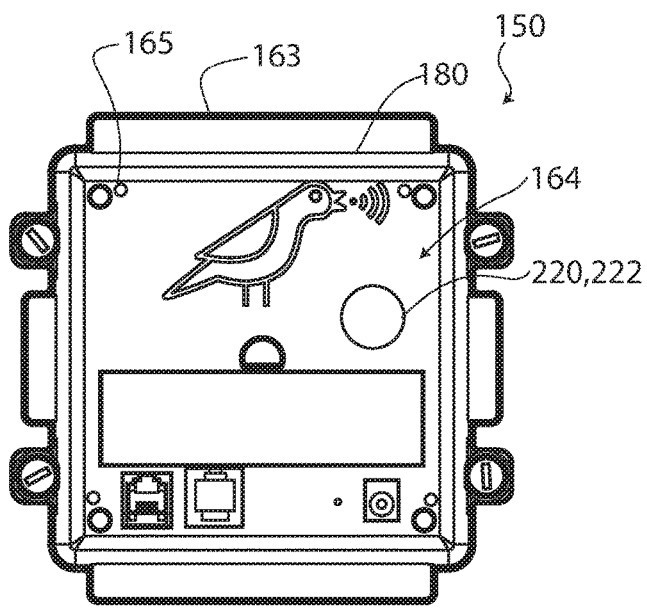
FIG. 11 is a bottom plan view of the electronics package of FIG. 10.
Figure 12:
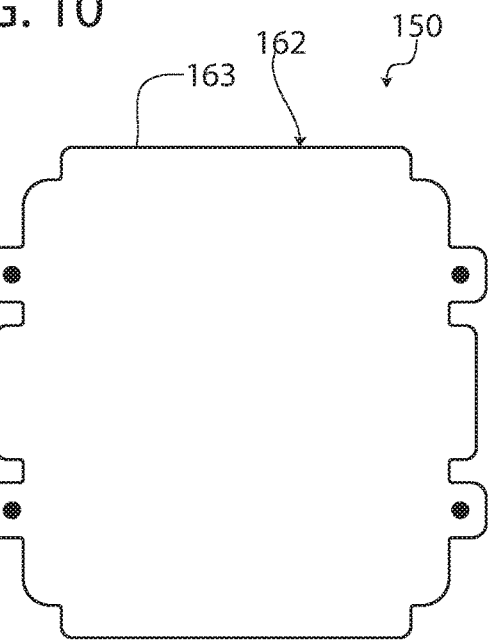
FIG. 12 is a top plan view of the electronics package of FIG. 10.
Figure 13:
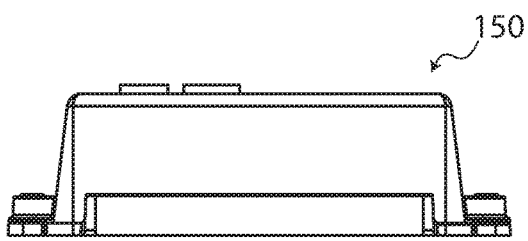
FIG. 13 is a side elevation view of the electronics package of FIG. 10.
Figure 14:
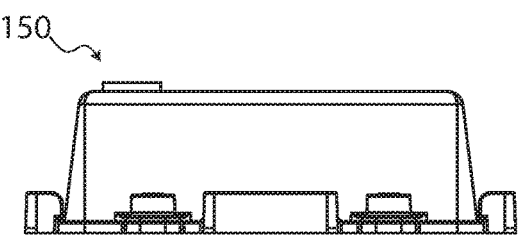
FIG. 14 is a side elevation view of the electronics package of FIG. 10.
Figure 19:
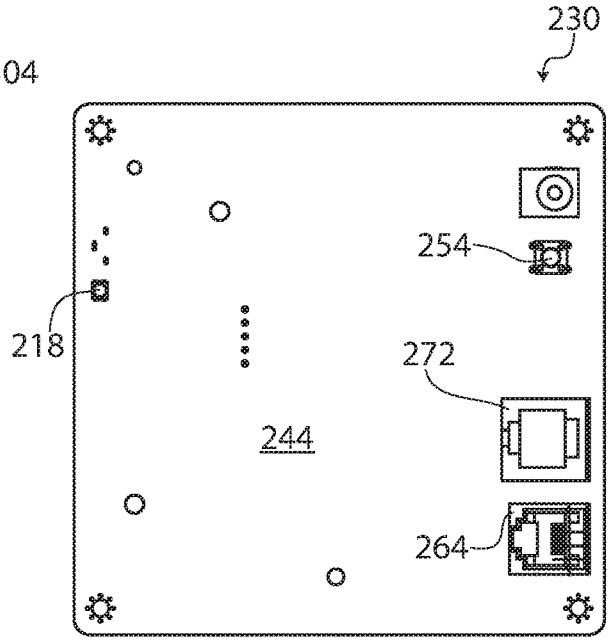
FIG. 19 is a bottom plan view of the electronics package of FIG. 16.

With reference to FIG. 19 illustrating a bottom plan view of the printed circuit board assembly 230, the back side 244 may have the analog switch 254 configured to receive a tool (e.g. a small piece of wire, not shown) through the housing 160 for a reset procedure while in service. As best shown in FIG. 19, the physical sample connector 272 and the metrological connector 264 may be universal connectors (e.g. telecommunications registered jack) for interfacing with remote devices such as the sampling devices 211 or the meteorological module 200. As best illustrated in FIG. 10, the physical sample connector 272, the metrological connector 264, and solar connection 252 extend to the outside portion of the housing 160.

Figure 20:
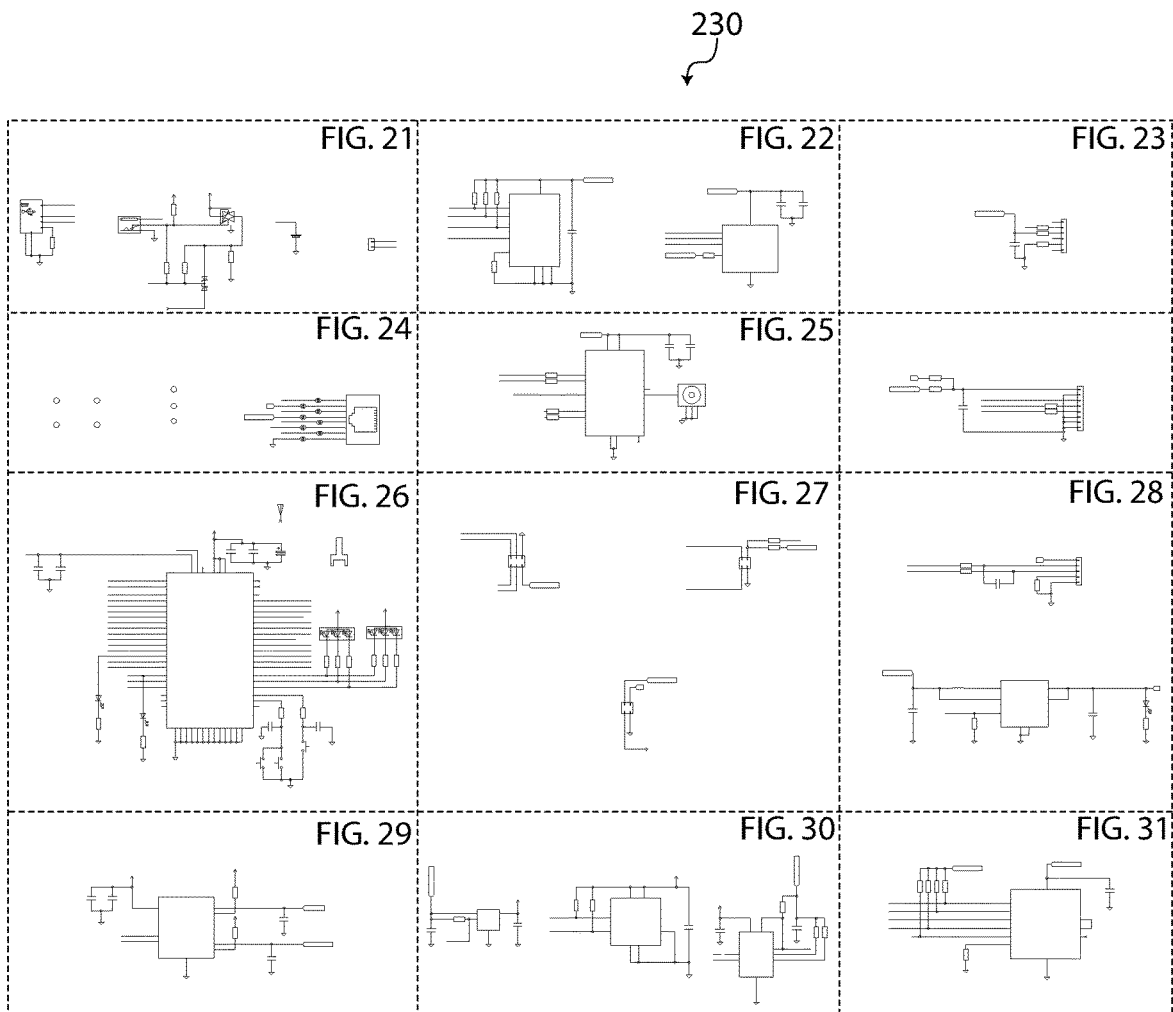
FIG. 20 is a schematic diagram of illustrative components of a pollution monitor noting additional figures with enlarged details, according to an illustrative embodiment of the present disclosure.

With reference to FIG. 20 illustrating a schematic of one configuration of the printed circuit board assembly 230, the details of optional and illustrative components are shown on FIGS. 21-31. While only some of these components may be utilized, others (not shown or described) may be implemented depending on the intended functionality of the pollution monitor. Therefore, the present printed circuit board assembly 230 described is illustrative and not necessarily the only configuration.

Figure 21:
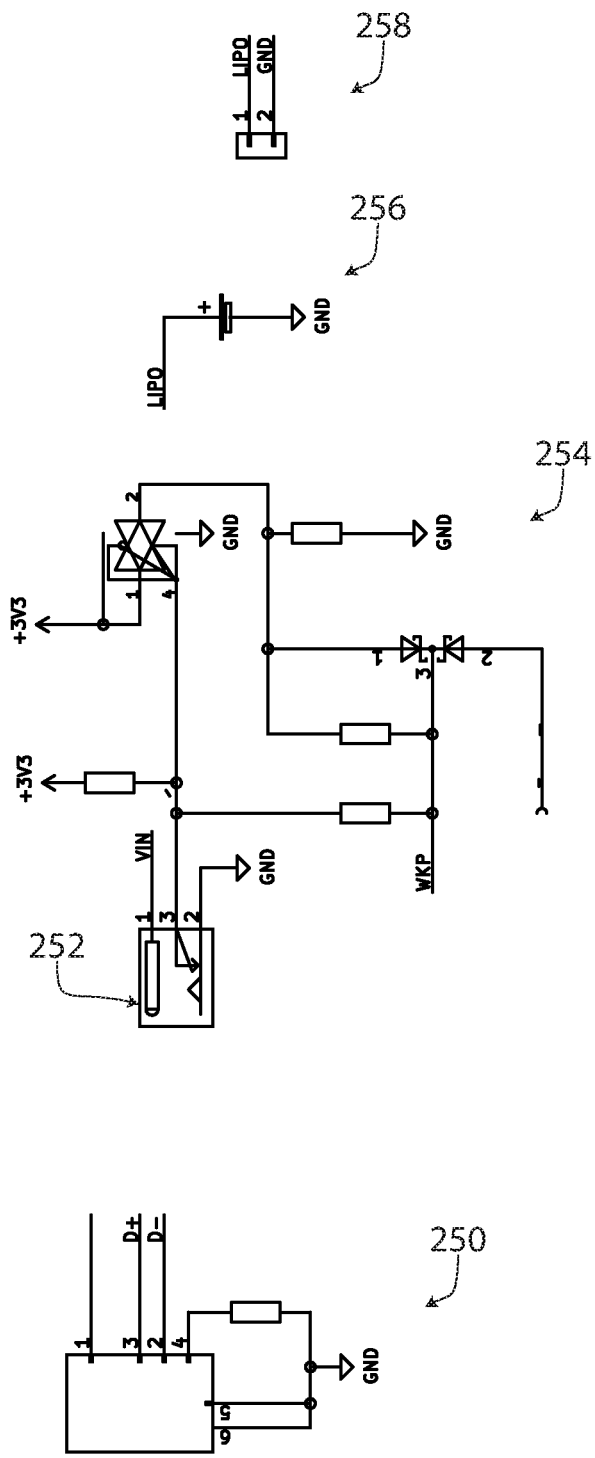
FIG. 21 illustrates input connectors of the schematic diagram of FIG. 20 including a USB connection, a solar connection, an analog switch, a battery holder, and a battery connector.

With reference to FIG. 21, the USB connection 250 may be a standard micro-USB connector commonly used in electronic devices. The solar connection 252 may be a commonly sourced barrel type connector for connecting DC power, such as the power supplied by the solar panel 140 (FIG. 3) via the power lead 146 (FIG. 3). The analog switch 254 may be provided for restarting, adjusting, or otherwise interfacing with the pollution monitor. The primary battery holder 256 and secondary battery connector 258 may be provided for receiving a power source. In one configuration, the secondary battery connector 258 may receive a primary (non-rechargeable) battery. For example, the secondary battery connector 258 may receive a large battery such as an absorbed glass mat lead-acid battery or it may receive a coin cell battery depending on the particular application for the pollution monitor.

Figure 22:
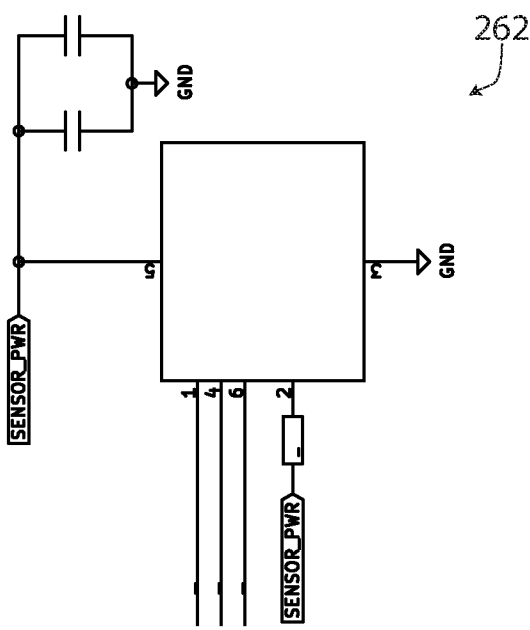
FIG. 22 illustrates meteorological sensors of the schematic diagram of FIG. 20 including a temperature and humidity sensor and a microphone.
Figure 22:
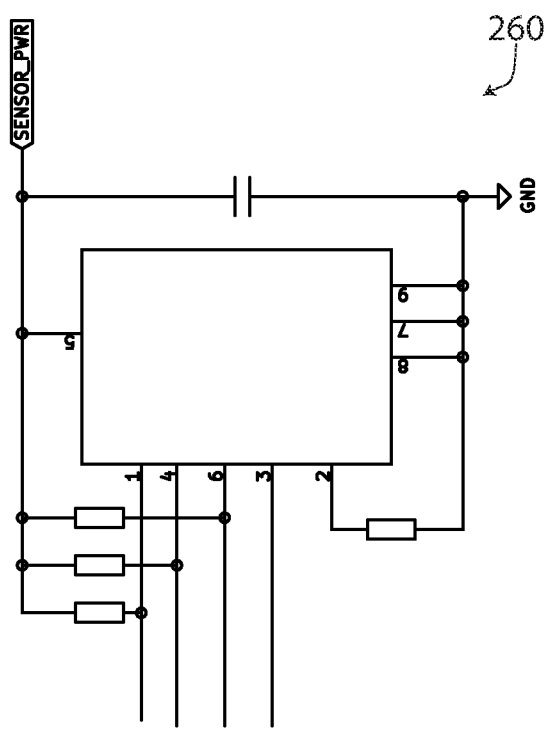

With reference to FIG. 22 illustrating the temperature/humidity sensor 260 and microphone 262, the temperature/humidity sensor 260 may be any of a number of types of sensors. In one illustrative example, the temperature/humidity sensor 260 may be a temperature/humidity sensor with multiple functions and various interfaces (12C, analog voltage output) that operates across a wide operating voltage range (2.15 to 5.5 V). The temperature/humidity sensor 260 may include enhanced signal processing, distinctive and user-selectable 12C addresses, an alert mode with programmable humidity and temperature limits, and communication speeds of up to 1 MHz. In one illustrative example the temperature/humidity sensor 260 may be a the Sensirion SHT31-D sensor with ±2% relative humidity and ±0.3° C. temperature accuracy. With continued reference to FIG. 22, the microphone 262 may be configured as a micro-sized I2S output microphone that can be used to digital record audio and be sent to an MCU/SOC in digital format without the need for any CODEC or additional hardware typically needed with an analog microphone. Output from the microphone 262 can be directly connected via I2S port and does not require any additional components such as a codec to provide digital audio. The microphone 262 may be configured to directly or indirectly report sound level, sound frequency, and/or spectrum density. One illustrative example of a microphone is the Sensor Maestros MIC-SPH0645LM4H-B.

Figure 23:
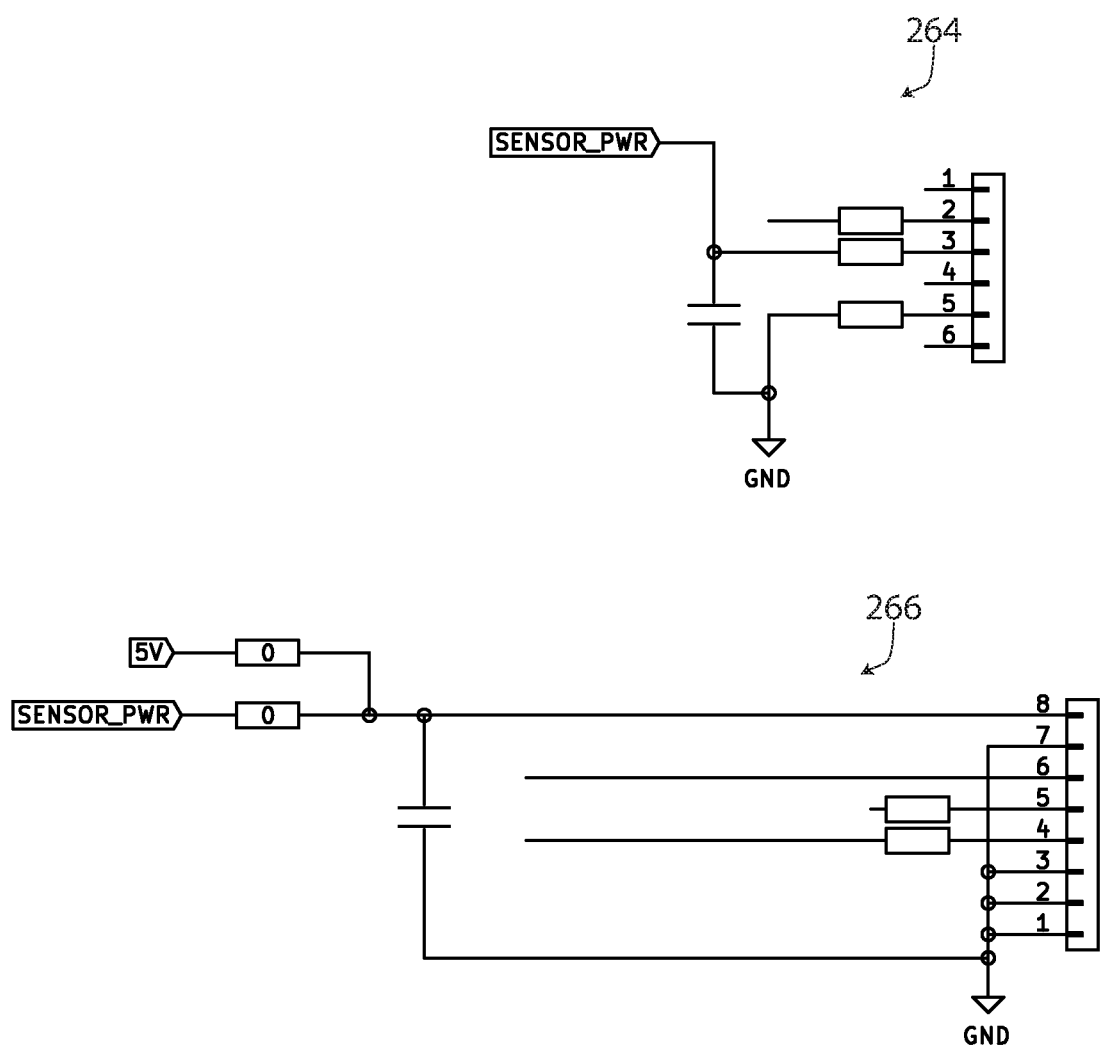
FIG. 23 illustrates pollution sensors of the schematic diagram of FIG. 20 including a methane sensor and an external environmental sensor.

With reference to FIG. 23, the metrological connector 264 may be connected to an external device capable of reporting environment conditions (weather) such as wind speed, wind direction, temperature, humidity, dew point, rain level, etc. In one configuration, the metrological connector 264 receives a device that presents three weather measurement: wind speed, wind direction and rainfall. The rain gauge may be a self-emptying bucket-type rain gauge which activates a momentary button closure for each 0.011 inches of rain that are collected. The anemometer (wind speed meter) may encode the wind speed by simply closing a switch with each rotation. And, a wind vane may report wind direction as a voltage which is produced by the combination of resistors inside the sensor. One example of this device is Sparkfun SEN-08942.

With continued reference to FIG. 23, the first pollution sensor 266 may be a methane sensor such as an infrared combustible gas sensor having an integrated system and includes mirror optical system, photodiode and LED, signal amplifiers, microcontroller, current driver of the infrared LED, UART interface signal generator and forming voltage supply unit. The sensor's microcontroller performs storage of unique sensor calibration constants, processing of measurement results and concentration of measured gas, and information exchange. One illustrative version of the first pollution sensor 266 operates according to a principle based on NDIR technology, i.e. on selective infrared radiation absorption by gas molecules. Infrared radiation from LED permeates through a measuring diffusion-type gas cell and arrives on signal and reference photodetectors, one of which detects radiation only in the wavelength range of infrared radiation absorbed by gases, while the other one detects radiation only in the wavelength range of 3.5 to 3.7 μm. Gas flowing through the cell absorbs the radiation of the operating wavelength and does not affect the radiation of the reference wavelength. One example of a sensor is the MIPEX-04 by Mipex Technology.

Figure 24:
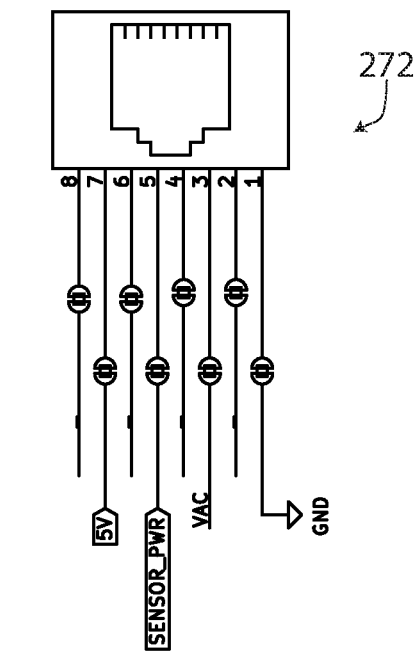
FIG. 24 illustrates miscellaneous components/features of the schematic diagram of FIG. 20 including mounting holes, fiducials, and a connector.

With reference to FIG. 24, the physical sample connector 272 may be a telecommunications registered jack commonly used in the telecommunications industry such as, for example, a typical RJ45 connector accessible from the outside of the pollution monitor. Other features are illustrated such as fiducials and mounting holes.

Figure 25:
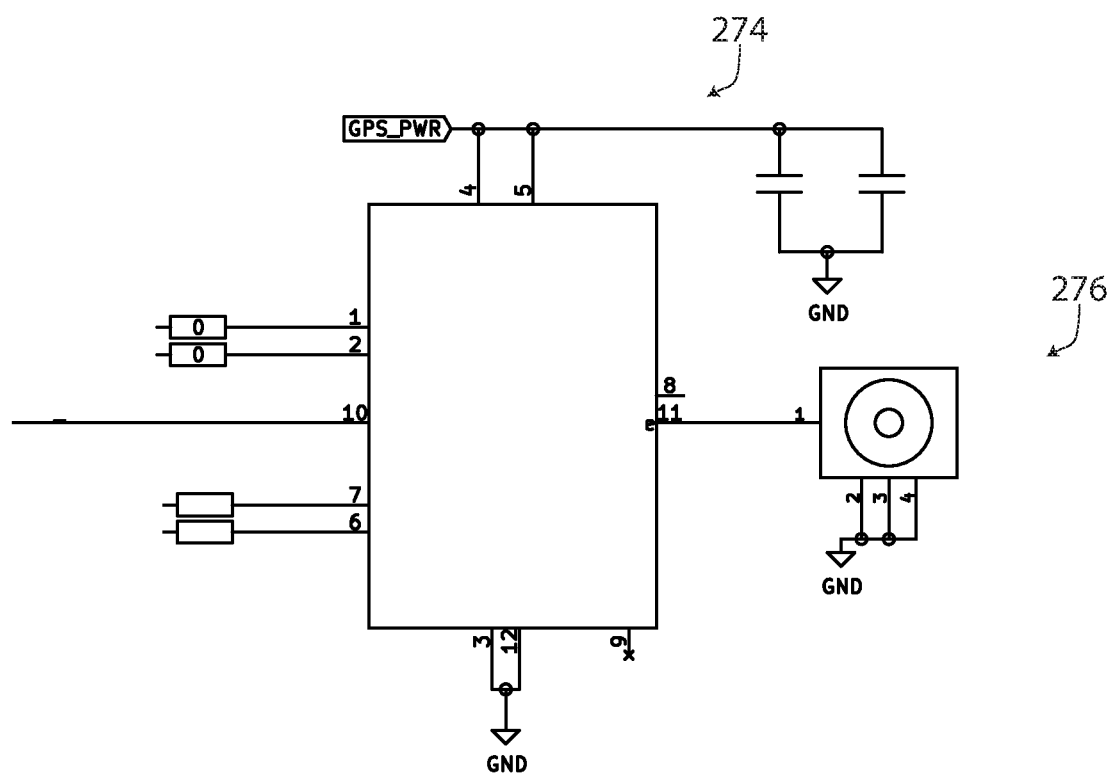
FIG. 25 illustrates a location sensor of the schematic diagram of FIG. 20 including a global positioning sensor (GPS)

With reference to FIG. 25, the location module 274 and location antenna connector 276 may be any of a variety of types of location devices, such as those using the global positioning system. Some examples of location modules are application specific and have an antenna integrated on the device that utilize technology to calculate and predict location satellite orbits automatically using the ephemeris data stored in internal RAM memory to enable the location module to quickly report a location without consuming much power. If the integrated antenna is insufficient for capturing a satellite(s) location, an external antenna may be used (via the location antenna connector 276). In one illustrative example, the location module 274 is a Quectel L80 GPS. As used herein, the term 'geolocation' is the identification or estimation of the real-world geographic location of an object. In its simplest form, geolocation may include generation of a set of geographic coordinates and is closely related to the use of existing positioning systems or simply as a street address. The word 'geolocation' may refer to the latitude and longitude coordinates of a particular location described by the standardized real-time locating system standard ISO/IEC 19762-5:2008.

Figure 26:
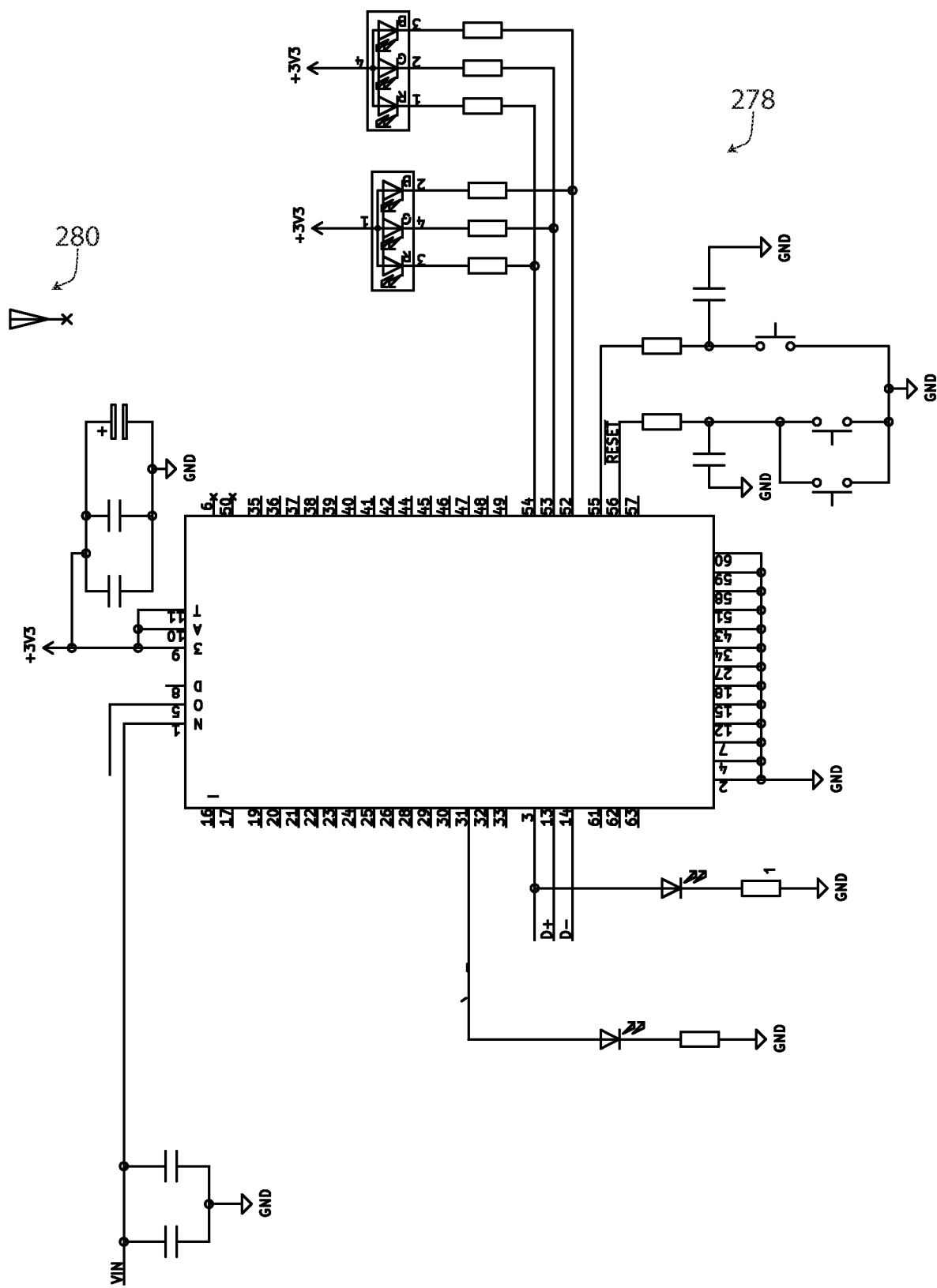
FIG. 26 illustrates a communications platform of the schematic diagram of FIG. 20 including a cellular protocol system, an antenna, and a status indicator.

With reference to FIG. 26, the communications module 278 and communications antenna connector 280 may be any of a variety of communication devices. In one embodiment, the communications module may be configured to communicate with other pollution monitors (e.g. by mesh, WiFi, cellular, satellite, etc.). The communications module 278 of the electronics package 150 may be any of a variety of communications devices ranging from infrared communications components (IR LEDs and photodetectors) to radio frequency communications components. While any of an almost infinitely large variety of communications protocols may be implemented, some particularly useful examples include Bluetooth, LORA, SIGFOX, SIGBE, satellite communications, particle.io, radio, TLE, CDMA, GSM, etc. If provided with the communications module 278 configured as a Particle.io device, the hardware may include a 120 Mhz ARM Cortex M3 microcontroller and a Wi-Fi chip. In one embodiment, the electronics package 150 may be updated via over-the-air firmware updates utilizing a protocol.

Figure 27:
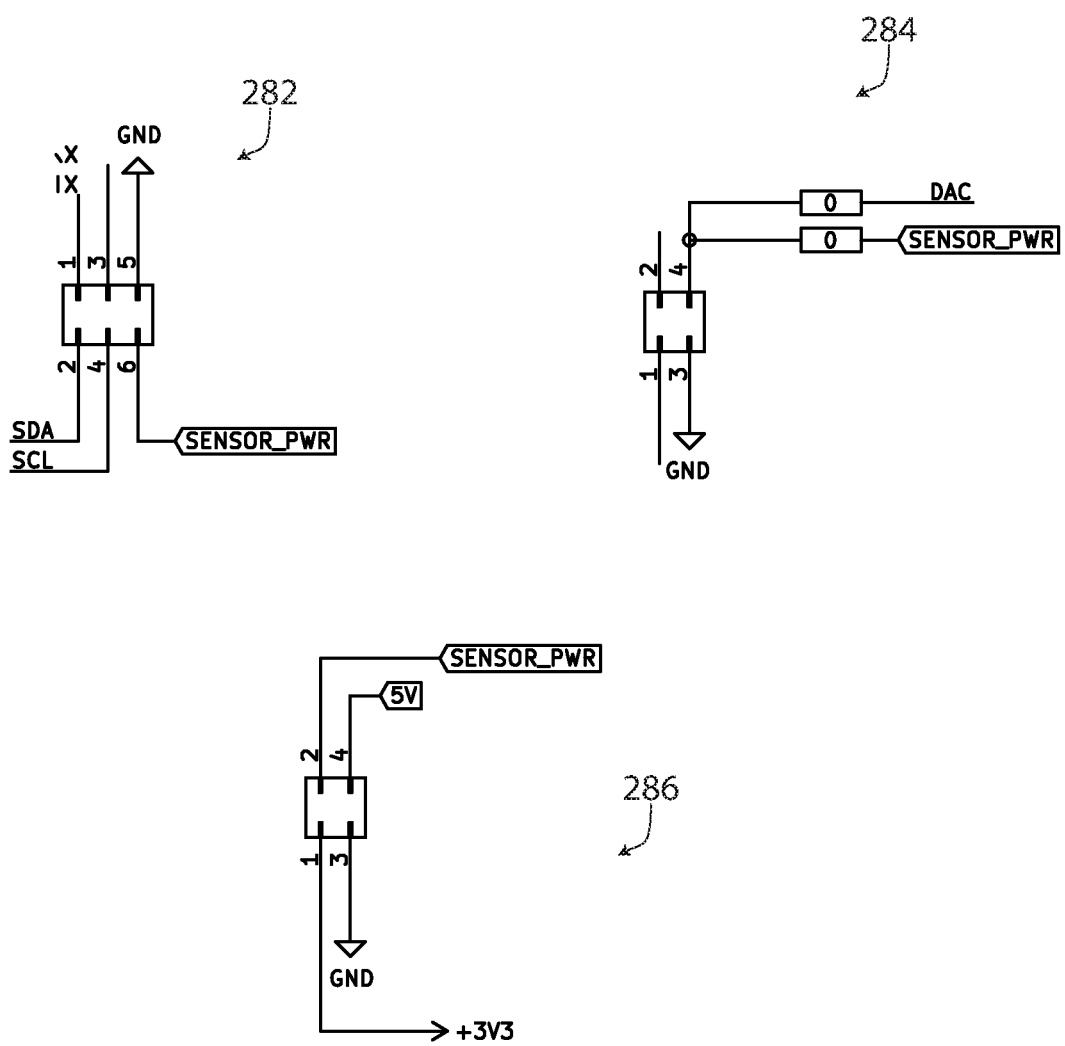
FIG. 27 illustrates expansion connectors of the schematic diagram of FIG. 20 including an analog expansion connector, a digital expansion connector, and a power expansion connector.

With reference to FIG. 27, the first expansion connector 282, the second expansion connector 284, and the third expansion connector 286 may be useful for future development/functionality. In one example, the first expansion connector 282 may be interfaced with the transmit and receive lines of the first pollution sensor 266 (e.g. the MIPEX-04 sensor). Further, the second expansion connector 284 may be interfaced with other pollution sensor if so desired.

Figure 28:
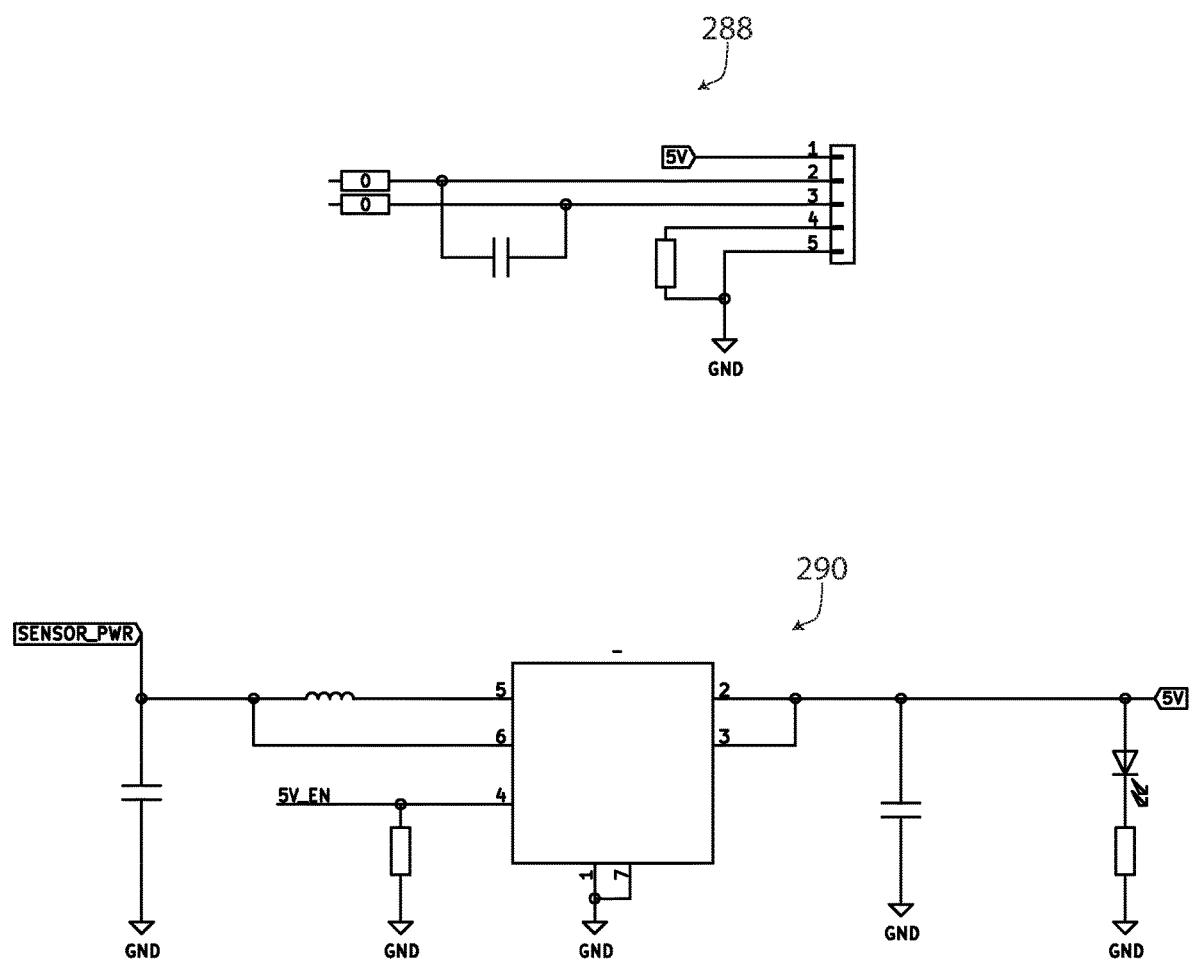
FIG. 28 illustrates miscellaneous components/features of the schematic diagram of FIG. 20 including an external particulate sensor and a boost converter.

With reference to FIG. 28, the fourth pollution sensor 288 and boost converter 290 may be provided for accurately determining particular matter in the atmosphere. For example, the fourth pollution sensor 288 may be configured as a sensor operating on the principle on laser scattering uses an innovative contamination-resistance technology. In one example, the fourth pollution sensor 288 may be configured as another Sensirion SPS30 to augment the other sensor provided in duplicity for accuracy, redundancy or life-span extension. If configured with a boost converter 290, the output voltage presented to a sensor (e.g. the fourth pollution sensor 288) may be accurate to the point that anomalies in the sensors output are nearly eliminated. On example of a boost converter 290 is Texas Instrument's TPS61240.

Figure 29:
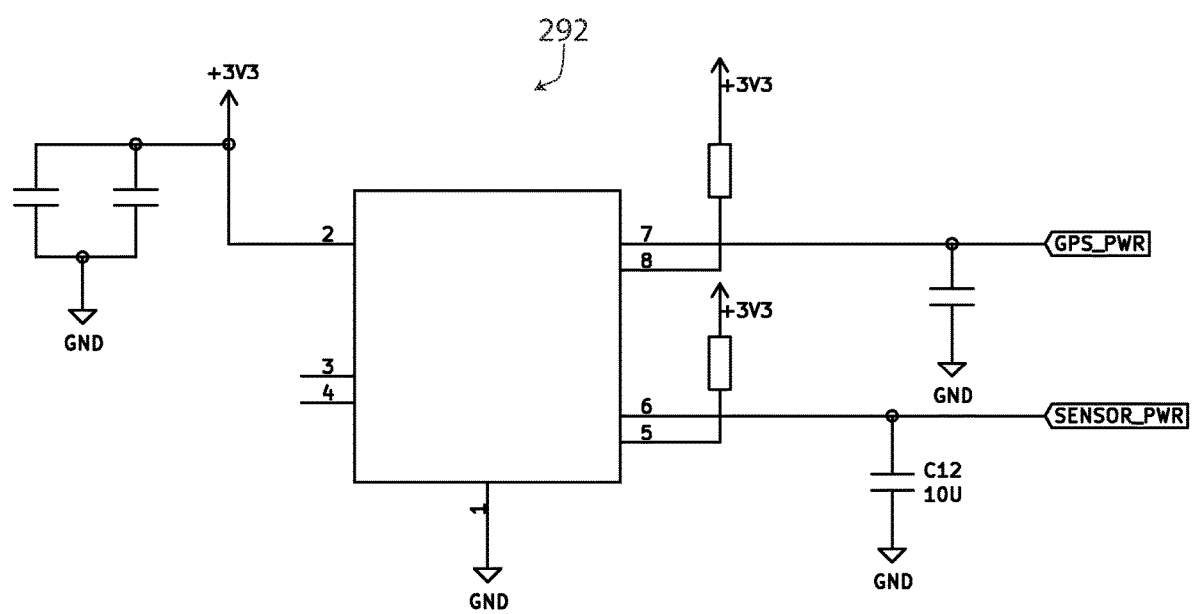
FIG. 29 illustrates power components of the schematic diagram of FIG. 20 including a power distribution switch.

With reference to FIG. 29, the power switch 292 may be provided to power sensors (e.g. pollution sensors) or other modules of the electronics package 150 (e.g. location module). One example of the power switch 292 is Texas Instruments TPS2052B.

Figure 30:
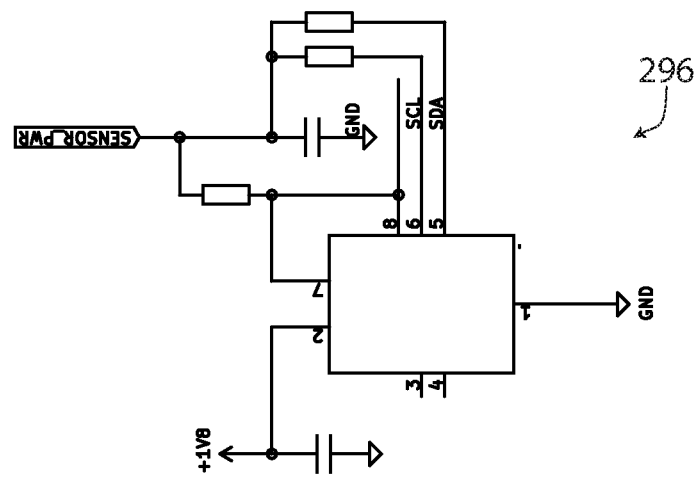
FIG. 30 illustrates miscellaneous components of the schematic diagram of FIG. 20 including a voltage-level translator, a pollution sensor (e.g. volatile organic compound sensor), and a voltage regulator.
Figure 30:
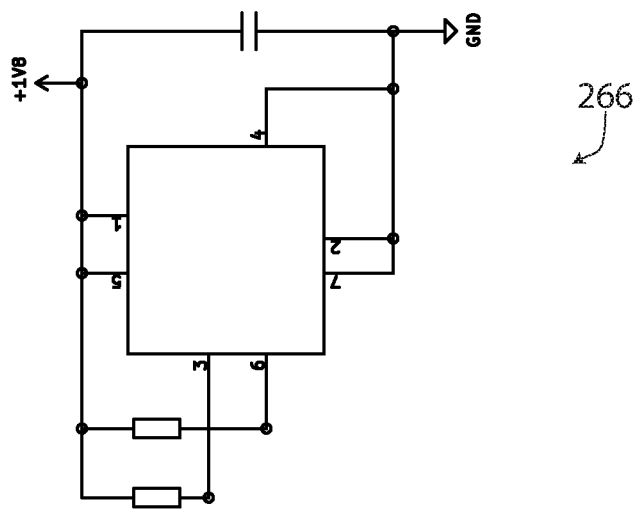
Figure 30:
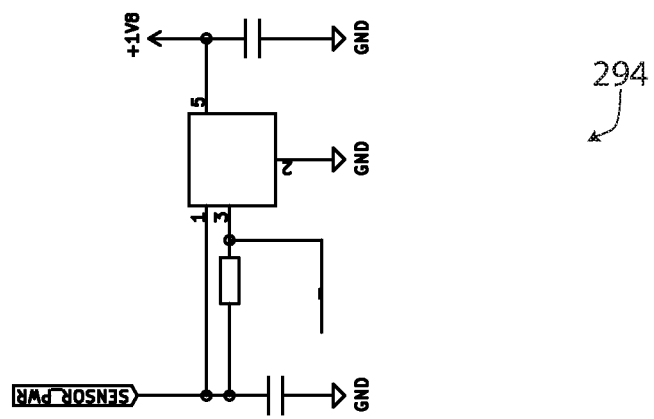

With reference to FIG. 30, the voltage regulator 294, the first pollution sensor 266, and the signal translator 296 may be provided for cooperating to measure a pollutant that is in the atmosphere. In some instances, the first pollution sensor 266 requires an accurate voltage and therefore the voltage regulator 294 may be utilized for improving the pollution signal emitted by the first pollution sensor 266. In an effort to further improve signal accuracy (and in some cases response), the signal translator 296 may be utilized to accelerate signal handling. The signal translator 296 may be a device that includes a dual bidirectional 12C and SMBus voltage-level translator with an enable input allowing bidirectional voltage translations between 1.2 V and 5 V, without the use of a direction pin. The low ON-state resistance of the switch allows connections to be made with minimal propagation delay. In one example, the voltage regulator 294 may be configured as the Diodes Incorporated AP2127K. In another example, the first pollution sensor 266 may be the Sensiron SGPC3. In another example, the signal translator 296 may be the Texas Instrument PCA9306.

Figure 31:
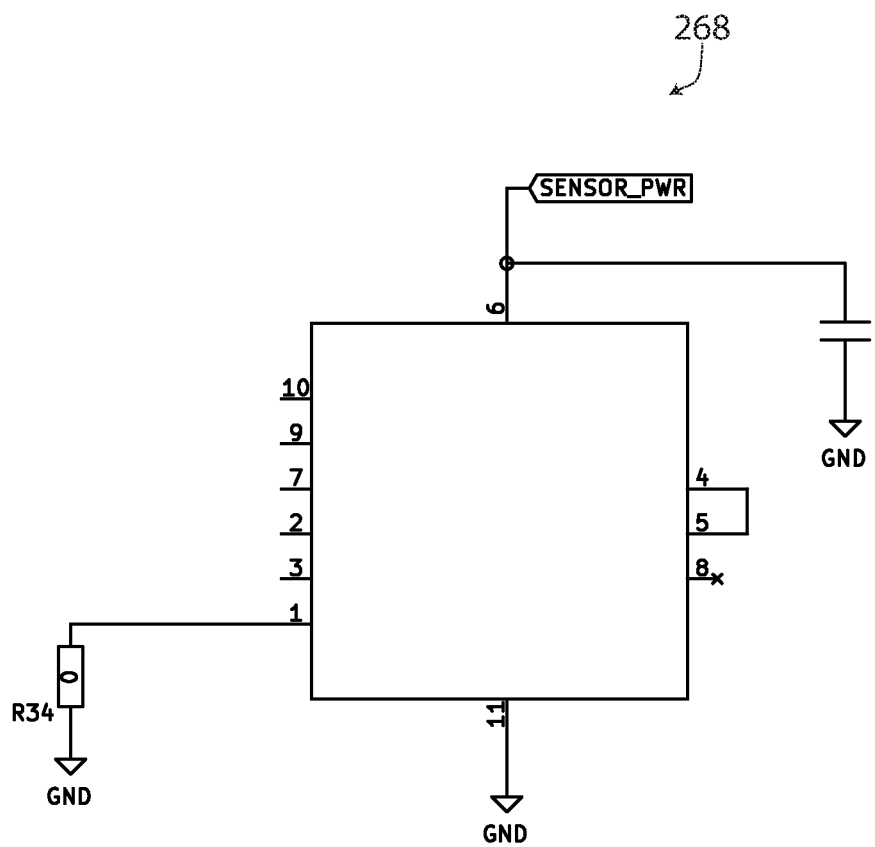
FIG. 31 illustrates a sensor of the schematic diagram of FIG. 20 including a pollution sensor.

With reference to FIG. 31, the second pollution sensor 268 may provide pollution detection and reporting pollution. In one example, the second pollution sensor 268 may be a low-power digital gas sensor solution which integrates a gas sensor solution for detecting low levels of VOCs. The second pollution sensor 268 may include a microcontroller unit (MCU) and an Analog-to-Digital (A/D) converter to monitor the local environment and provide an indication air pollution via an equivalent CO2 or total VoC output over a standard I2C digital interface. In one example, the second pollution sensor 268 may be an AMS CCS81.

Having described various embodiments of apparatus for reducing fugitive emissions at oil facilities, various illustrative methods of reducing fugitive gas emissions and other features will now be presented.

Figure 32:
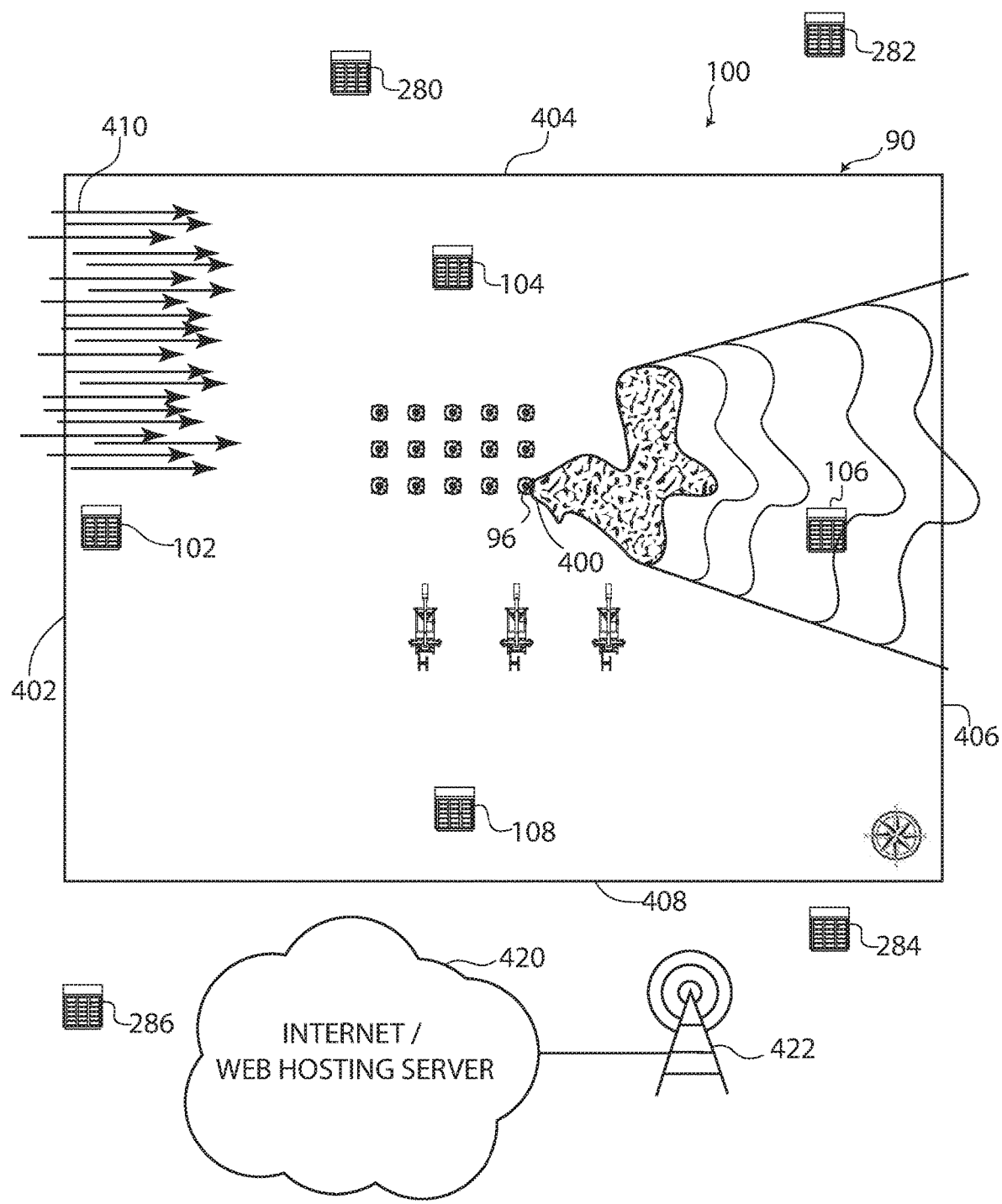
FIG. 32 is a top plan view of an oil facility (e.g. a wellsite) having an emissions source (also referred to as a leak, a leak event, etc.), the oil facility is monitored by an illustrative configuration of a plurality of pollution monitors, according to an illustrative embodiment of the present disclosure.

With reference to FIG. 32 illustrating a top plan view of an oil facility experiencing a leak (sometimes referred to as an emissions source 400), the oil facility is monitored by at least one pollution monitor (e.g. 102, 104, 106, or 108). The illustrated example utilizes four pollution monitors: the pollution monitor 102 positioned at a West boundary 402 of the monitored area 90; the pollution monitor 104 positioned at a North boundary 404 of the monitored area 90; the pollution monitor 106 positioned at an East boundary 406 of the monitored area 90; and, the pollution monitor 108 is positioned at a South boundary 408 of the monitored area 90. Wind 410 (illustrated as directional arrows) is a mass of ambient air moving from the West towards the East. This idealized illustration is a snapshot in time, and it is understood that wind is rarely unidirectional as illustrated-however this illustration conveys some principles of the present disclosure. As the wind 410 moves into the monitored area 90 at the West boundary 402, the pollution monitor 102 reads a property of the ambient air via the pollution sensor 202 in the electronics package 150 (both in FIG. 6). As the wind 410 continues across the monitored area 90, any matter added to the wind 410 increases the pollution. For example, if the emissions source 400 is leaking hydrocarbons in the atmosphere, the wind 410 will 'gain' in hydrocarbons. This gain may be detected by the system that utilizes pollution monitor 106 and the pollution sensor 202 of the electronics package 150 (both in FIG. 6).

With continued reference to FIG. 32, readings from the individual pollution sensor 202 in the pollution monitors 102 and 106 may be interpreted by the logic control system 190 (FIG. 8) and may be transmitted to an internet-attached web hosting server 420 via the communications module 204 (FIG. 15) and a communications tower 422. When the sensor readings are compared (either at a local-level inside one or more of the pollution monitors, at/on the internet-attached web hosting server 420, etc.), the emissions source 400 is detected and located. With this detection and/or location, an operator (or other interested party) of the monitored area 90 can be notified for any of a variety of actions including, but not limited to, opening a troubleshooting ticket, adding field service to an upcoming maintenance list, initiating a truck-roll to the monitored area 90, or a variety of other actions depending on predetermined thresholds and/or remedy actions.

While FIG. 32 shows the wind 410 moving from the West to the East (i.e. Westerly wind), in reality the wind moves from the West, to the North, to the South, and generally in all directions. Therefore, the present oil facility 100 is configured to receive data from the various pollution monitor 102, 104, 106, 108 and to process (e.g. average or otherwise interpret/process) the results to increase confidence of the findings. The utility of the clock module 224 (FIG. 15) may be that each snapshot of data is timestamped. The timestamped data may be utilized to accurately assess the operation of the event and to clearly know conditions inside and around the monitored area 90.

Figure 33:
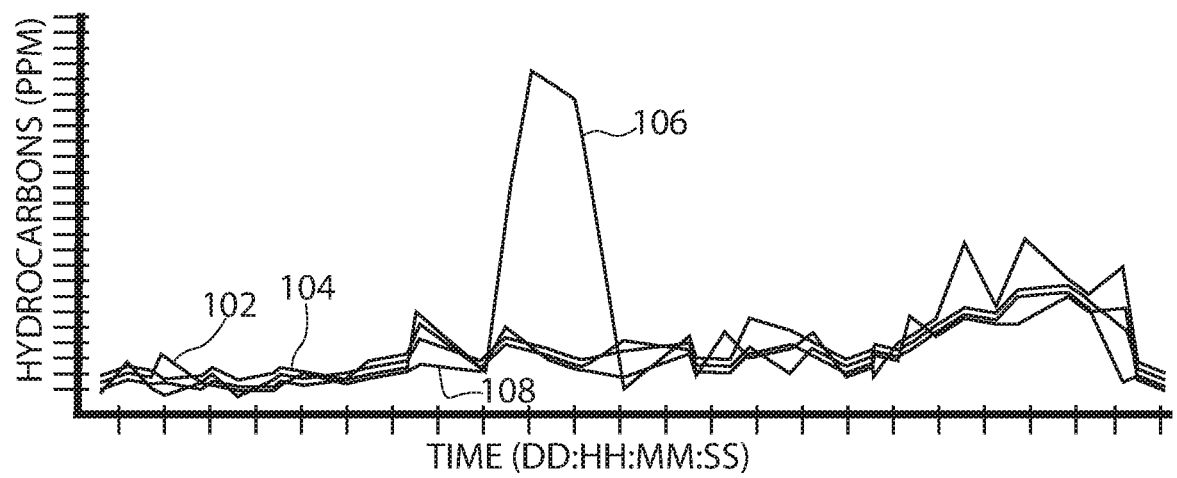
FIG. 33 illustrates a graph of outputs from the plurality of pollution monitors of FIG. 32.

With reference to FIG. 33 illustrating a graph of sensor outputs from a plurality of pollution monitors (e.g. 102, 104, 106, 108), the graph shows one particular pollution as hydrocarbons in parts per million (PPM) graphed against time. For example, if the same event from the description of FIG. 32 is represented on the present graph, the outputs from pollution monitor 106 will spike during presence of the emissions source 400 (FIG. 32). Once the emissions source 400 terminates (either by repair or other change), the reading drops to the ambient level as illustrated.

In one illustrative configuration, a method for reporting atmospheric pollution may include steps to perform the reporting. In a first step, a first pollution monitor 102 and a second pollution monitor 106 may be installed in (or around) a monitored area 90. In a second step, the pollution levels present (and sensed) at the first pollution monitor 102 and the second pollution monitor 106 are sensed and compared. During normal operation of the two different pollution monitors, 102, 106, the pollution sensor 202 (FIG. 6) in each pollution monitor 102, 106 sense and report a presence of matter such as hydrocarbons in parts per million. During a third step, the readings of atmospheric pollution originating at the oil facility are reported. A leak may be detected in a number of ways such as: a predetermined threshold is reached (and the confidence is high that there is a valid reading indicating presence of the emissions source 400); or, exceeding a threshold (differential concentration) and occurring over a duration (how long has the leak been going on) as criteria for generating a report (alert via SMS or email) of a possible leak condition. It is worth noting that as the wind direction changes during a leak event and therefore the reading of a sensor may decrease, but the larger system may continue to treat the leak event as continuous for the sake of meeting the 'duration' criteria. Differentiating between normal field operations and actionable emission events may require sophisticated algorithms (e.g. conventional statistical analysis and/or more nuanced applications of machine learning). These algorithms may be updated before deployment or during operation through coordinating with field operations facilities to guide the system by integrating site service records into the emissions data stream. Once a leak is determined, the reporting may commence (e.g. through an alert via SMS, Email, or other communications platform). During the reporting step, the operator of the monitored area 90 may be notified for any of a variety of actions including, but not limited to, opening a troubleshooting ticket, adding field service to an upcoming maintenance list, initiating a truck-roll to the monitored area 90, or a variety of other actions depending on predetermined thresholds and/or remedy actions. In order to reduce false-positive events, the readings from the pollution monitors 102, 104, 106, 108 may be average-adjusted to compensate for initial discrepancies in the pollution sensor 202 readings or differences that evolve over time due to unique performance characteristics that may not be accounted for during the initial production or qualification of each individual pollution sensor 202. For example, each individual pollution sensor 202 from each of the pollution monitors 102, 104, 106, 108 can be compared to establish what is the baseline reading for each pollution sensor 202. This comparison may, for example, occur via peer-to-peer communication via the communications module 204 or in the internet-attached web hosting server 420.

Figure 34:
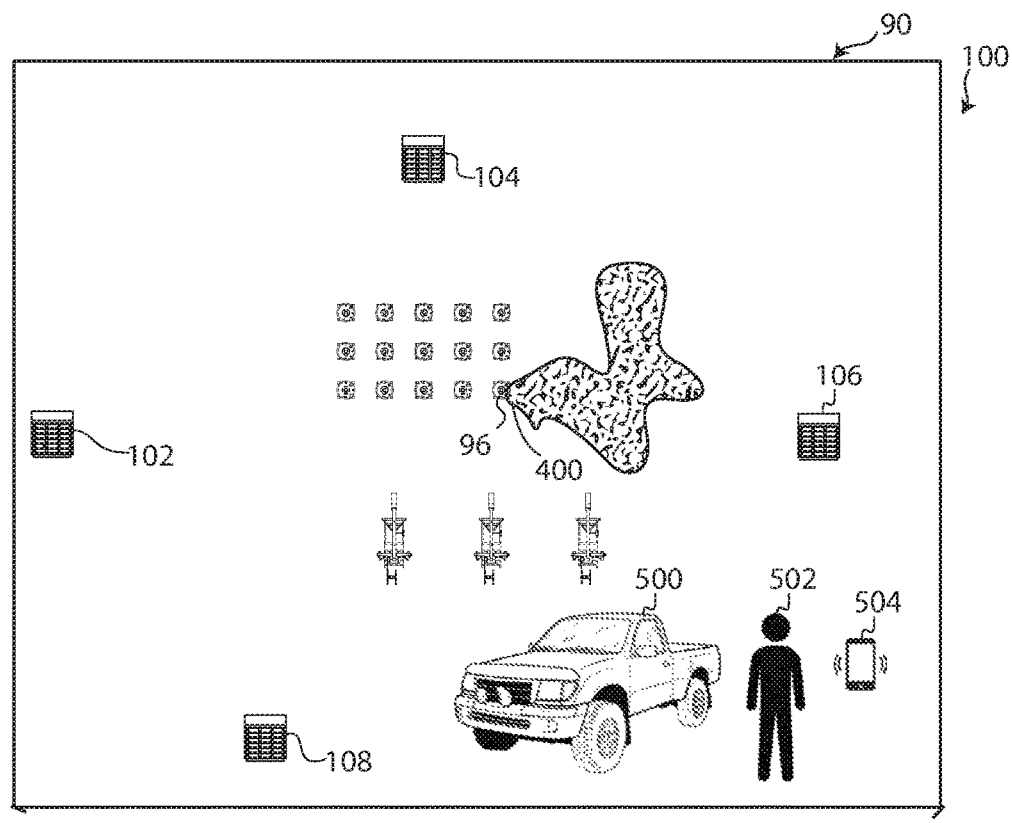
FIG. 34 is a top plan view of a rural oil facility and an illustration of a vehicle carrying a technician and a mobile device to/from the rural oil facility, according to an illustrative embodiment of the present disclosure.
Figure 34:
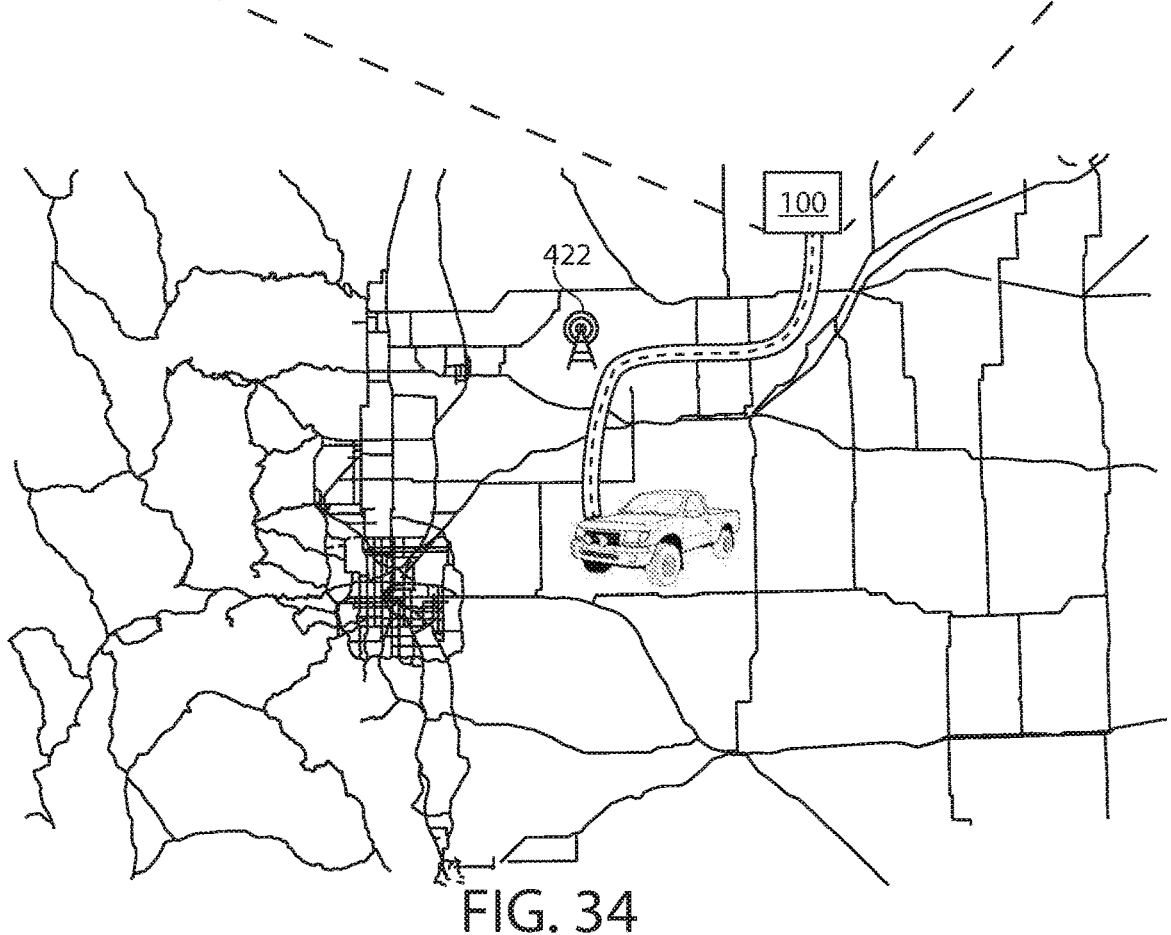

With reference to FIG. 34 illustrating a geographic area and a rural oil facility, the rural oil facility may be relatively far (e.g. 100 miles) from a home-location for a repair technician. Therefore, when a leak (e.g. holding tank 96 may have a faulty valve, for example) is detected and reported, a vehicle 500 may be deployed to carry a technician 502 and a mobile device 504 to repair the leak at the rural oil facility. In this illustration, the pollution monitor 106 (or other parts of the system) may emit a signal indicating elevated levels of a pollutant. The signal representing an elevated level is checked against a set of rules to determine if there is likely a leak. If the rules are met and therefore there is likely a leak, the system requests/instructs that a leak be repaired. In doing so, the system may send the repair instruction to the mobile device 504, thereby informing the technician 502 about the leak and requesting the technician 502 activate the vehicle 500 for travelling to the oil facility 100.

In one illustrative configuration, a method for activating a truck to move a technician to a rural oil facility as part of a process for repairing a leak, the pollution monitor is deployed at the oil facility and activated to monitor a signal representing atmospheric presence of at least one component of natural gas. In one illustrative embodiment, the sensor that produces this signal may include a hotplate and metal oxide semiconductor that changes resistance in presence of the component of natural gas. Once the signal is received, it is compared to a set of rules. The rules may be as elementary as crossing a threshold, or they may be more complicated and derived over time from machine automation (sometimes referred to as artificial intelligence, AI). This comparison may happen onboard the pollution monitor 106 or at a remote location (e.g. the internet/web hosting server 420) after the signal data is sent wirelessly. After comparing, the instruction to repair may be invoked. While many different repair instructions/actions may take place, one repair might require a vehicle to be activated to bring a repair technician to the rural oil facility to repair the leak. It is noted that any of the activities herein that are manual may have an underlying machine instruction leading up to the manual activity; this machine instruction may come in the form of a ticket, job order, text message, email, report, etc. indicating that the manual activity is to be implemented.

Figure 35:
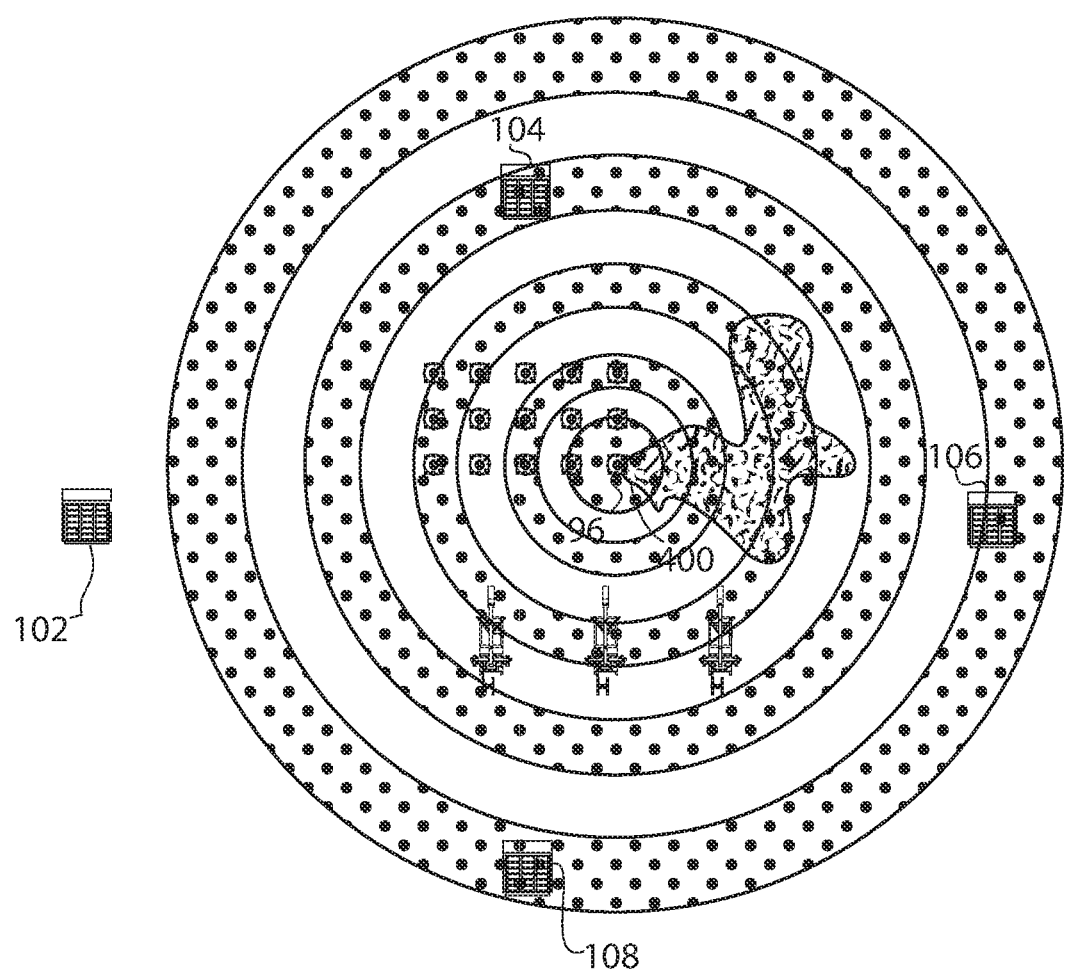
FIG. 35 is a top plan view of an oil facility with an illustrative pollution monitor system illustrating sound transfer from a leak to pollution monitors, according to an illustrative embodiment of the present disclosure.

With reference to FIG. 35 illustrating a top plan view of an oil facility with a pollution monitor system, sound emitting from a leak travels to pollution monitors of the pollution monitor system. An emissions source 400 emits noise as it leaks into the atmosphere due to its relatively high energy level (e.g. high heat and/or pressure). As this noise travels from the emissions source 400 to the pollution monitors (e.g. 102, 104, 106, 108), it is absorbed by various objects or otherwise dissipated into the environment. Therefore, the sound level of this noise is represented by concentric rings from the emissions source 400. To be clear, the noise level immediately adjacent to the emissions source 400 may be relatively high (e.g. 110 db) and taper off at locations away from the emissions source 400. When the emissions source 400 is located at different distances from the pollution monitors, the sound levels measured by the pollution monitors vary. As illustrated, the level of sound received at the pollution monitor 104 are different than the level of sound received at the pollution monitor 108. As illustrated, the noise level at pollution monitor 106 is higher than the noise level at pollution monitor 102. Through a process of vectoring, the location of emissions source 400 can be determined. As used herein, the term 'vectoring' may refer to acoustic source localization of a sound source given measurements of the sound emitting from an object/location (e.g. emissions source 400). The sound can be described using physical quantities (e.g. sound pressure and particle velocity). By measuring these properties it may be possible to obtain a source direction. Sound pressure (i.e. sound level) may be measured using a microphone having an omnidirectional polar pattern (sensitivity is independent of the direction of the sound). When a number of microphones are used, it is possible to locate a sound source through comparing sensed sound levels.

The above description of apparatus and methods are just illustrative embodiments provided for descriptive purposes. Other embodiments have been contemplated, such as the following alternatives.

In one alternative configuration, a method for transferring stored data representing pollution levels from a rural oil facility to a data center movement of a truck and transfer of the data via a communications protocol. This method for transferring data from a rural oil facility to a data center may commence by provisioning a pollution monitor at the rural oil facility. This provisioning may, for example, include driving a vertical object (e.g. a T-post) into the ground and attaching the insulating body 110 with the electronics package 150 to the t-post. It may place a pollution sensor in electrical communication with the electronics assembly 150 wherein the pollution sensor is configured to report a signal representing atmospheric presence of at least one component of natural gas. In the present description, the rural location may be 'off-network' whereby the wireless communication may be difficult if not impossible (for example, cellular data might not be available or too costly). At any rate, the signal data can be stored until a mobile device (also referred to herein as an electronic device) arrives at the oil facility. Once the mobile device is received at the oil facility via a vehicle, the stored signal can be transferred to the mobile device. In due course, the technician drives with the mobile device to a connected environment (e.g. a location where cellular data is present, or where a WiFi signal exists). At this point, the signal data can be transferred via at least one communication protocol. The method may be useful for locations where a communication protocol is difficult or impossible, but still provides a method for removing data from the oil facility.

In another alternative configuration, a method for locating a leak at an oil facility by vectoring the sound levels originating at the leak may begin by provisioning at least three pollution monitors. Each of the pollution monitors may be provided with a sound module (e.g. a microphone as described herein) configured to output a signal representative of the level of sound it is exposed to. The signals are sent from a pollution monitor and received (e.g. by one pollution monitor, a shared resource, or an offsite computer). The signals are used to locate the leak by comparing the signals in a process referred to as vectoring. In this process, the relative strength of a signal is utilized to triangulate in on the location of the emissions source 400.

In another alternative configuration, a method for identifying a leak at an oil facility by analyzing signal frequency may begin by provisioning a pollution monitor with a sound meter configured to output a frequency signal. Once the signal is sent and received, it is analyzed against a set of frequencies representing sounds emitting from leaking components. In an oil facility, there are a number of devices that have unique properties. Some of these devices are made of 'lively' materials (e.g. brass) ringing at a high frequency while others are made of relatively 'dead' materials (e.g. ductile iron). Therefore, when one of these devices is experiencing a leak nearby or, in one example, from the device, they emit a sound with a unique signature frequency. For example, a leaking solenoid valve may emit a loud screeching noise while a section of leaking pipe may emit a bass-like rumble. Ultimately, a determination of the leaking component may be made based on the analysis of the frequency of the sound. This may help to repair technician to be properly provisioned with repair materials and/or tools when they arrive at the oil facility to repair the leaking device.

In another alternative configuration, a method of locating a leak by comparing phase-arrival of signal may begin by provisioning a plurality of pollution monitors. Sound meters are included with pollution monitors that are capable to output a signal that represents arrival of a phase of the soundwave. The signal representing the phase arrival are received from the pollution monitors and compared to determine the location of a leak. As processors and sound meters improve, their sensitivity and speed may enable timely detection of phase arrival times. In accurately comparing arrival of a phase of sound, it may be possible to determine the distance and relative location of a sound source (e.g. a leak).

Figure 36:
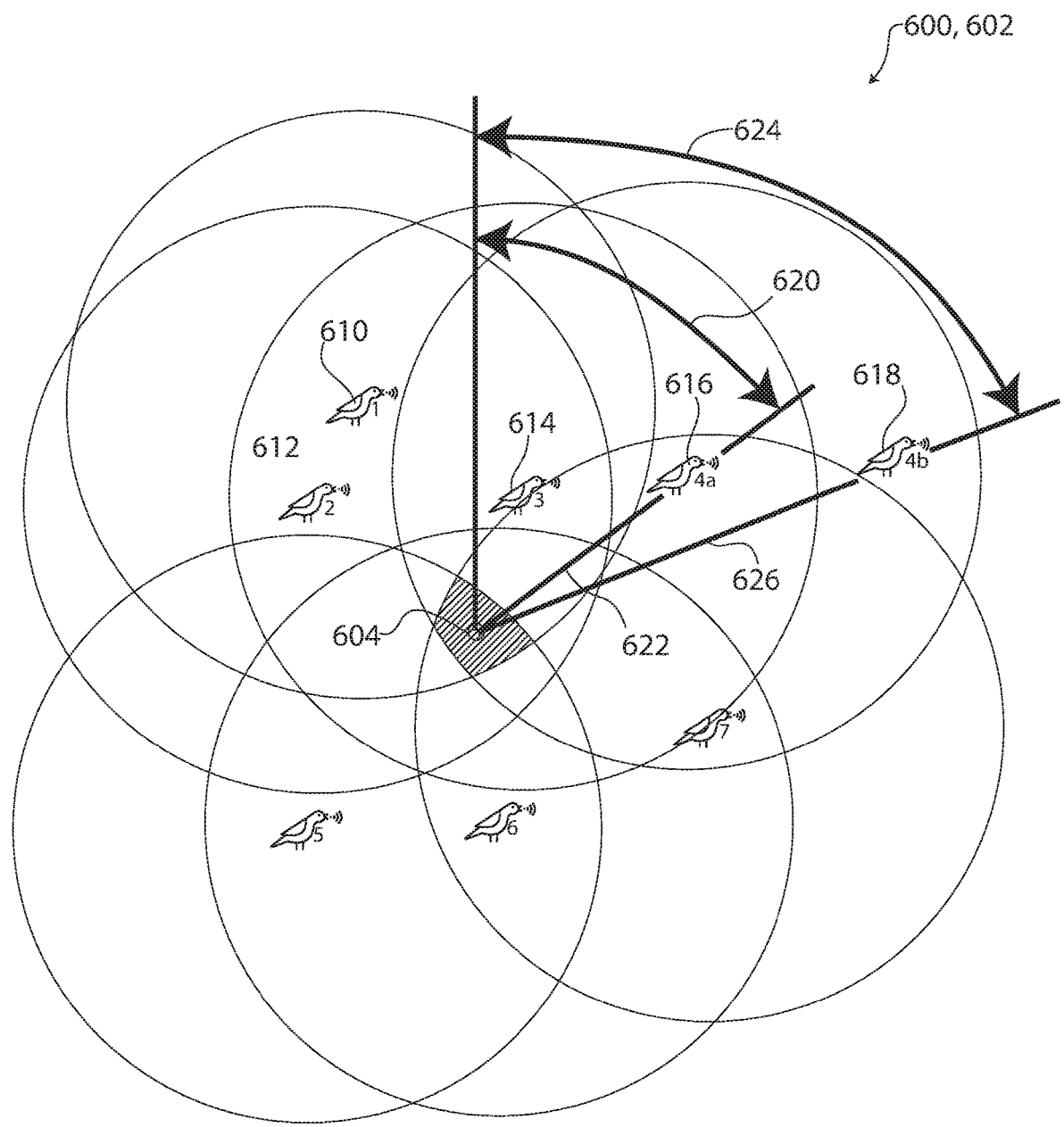
FIG. 36 is a top plan view of an oil facility configured with a pollution monitoring system, according to an illustrative embodiment of the present disclosure.

In another alternative configuration illustrated in FIG. 36 showing a top plan view of an oil facility 600 configured with a pollution monitoring system 602, a plurality of pollution monitors may be deployed at the oil facility 600 surrounding a centroid 604. For example, a first pollution monitor 610 may generally be located at a North-Northwest (N-NW) location relative to the centroid 604. A second pollution monitor 612 may be located at a Northwest (NW) location relatively to the centroid 604. A third pollution monitor 614 may be located at a North location relatively to the centroid 604. A fourth pollution monitor 616 may be located at a Northeast (NE) location relatively to the centroid 604. A replacement pollution monitor 618 may be located at the Northeast (NE) location relatively to the centroid 604. Additional pollution monitors may be positioned as illustrated relative to the centroid 604. In some a process that will be described herein, the pollution monitors may need to be replaced occasionally. For example, the fourth pollution monitor 616 may be hit by a service vehicle or for some other reason require replacement. The fourth pollution monitor 616 may be located at a first bearing 620 and a first distance 622 from the centroid 604. The first bearing 620 may be defined as an angle relative to due North, for example, as illustrated. The first distance 622 is a unit of measure from the centroid 604. When (or earlier, e.g. during initial provisioning) the damaged fourth pollution monitor 616 is replaced, this first bearing 620 and first distance 622 are noted. When the replacement pollution monitor 618 is deployed, it may not be necessary to position it exactly at the same first bearing 620 and first distance 622. In one example, the replacement pollution monitor 618 may be located at a second bearing 624 and a second distance 626 that is different than the first bearing 620 and first distance 622, respectively. However, for the purposes of monitoring the oil facility 600, the replacement pollution monitor 618 can be referred to as the Northeast location when provisioned at the second bearing 624 and the second distance 626.

In another alternative configuration, a method of provisioning a replacement pollution monitor at an oil facility may begin by noting an original location of a first pollution monitor. During the provisioning of a second pollution monitor, a bearing and distance of the second pollution monitor may be recorded. The bearing and distance of the second pollution may be compared to the first location monitor (e.g. its bearing and distance from a centroid). If the second pollution monitors bearing and distance comply with a predetermined set of rules, the second pollution monitor receive the location identifier of the first pollution monitor, and the first pollution monitor may be decommissioned. Even though the second pollution monitor is located at a slightly different location, it can be provisioned into the pollution monitoring system 602 having the same location identifier as the first pollution monitor. It has been found that a certain amount of tolerance is useful and/or required when replacing a pollution monitor. This maintains the database legacy and forward looking data rules and actions that rely on data from the first pollution monitor and any of its replacements.

Figure 37:
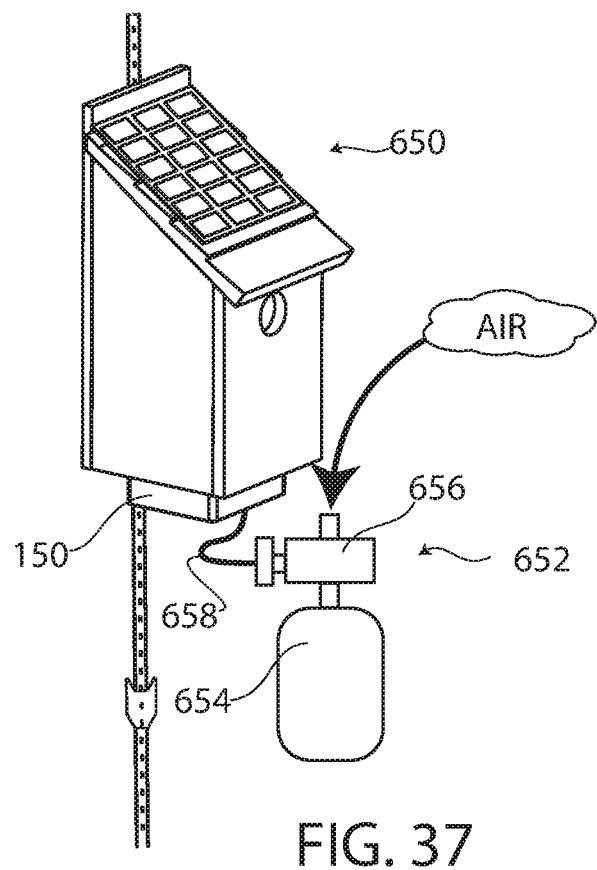
FIG. 37 is a perspective view of an illustrative pollution monitor configured with an optional physical sampling system (e.g. an air sampling system configures as a summa canister), according to an illustrative embodiment of the present disclosure.

In another alternative configuration in FIG. 37 showing a perspective view of a pollution monitor 650 configured with an optional physical sampling system 652 configured to capture a physical sample (e.g. air sample 212, soil sample 214, water sample 216, FIG. 15). The physical sampling system 652 may be configured to sample air via any of a variety of sampling devices known. For example, U.S. Pat. No. 3,866,474 to Hasselman describes a system in which a sample and an inert gas are drawn into a sample bag within a hermetically sealed container. U.S. Pat. No. 3,965,946 to D'Alo describes improvements to an outer container for sample air. U.S. Pat. No. 5,437,201 to Krueger describes a method of repeatedly purging the sampling bag within the outer container. U.S. Pat. No. 5,714,696 to Yemans describes a system for sampling air. U.S. Pat. No. 6,338,282 to Gilbert describes an apparatus for collection air. U.S. Pat. No. 6,993,985 to Srebro describes using the apparatus combined in single device yet connected to external vacuum source. U.S. Pat. No. 4,546,659 to Gill et al. describes a small (10 ml) envelope for the collection of atmospheric air samples for subsequent analysis. All of the above patents are specifically incorporated by references for all they disclose. In one illustrative configuration, the physical sampling system 652 includes a collection device (e.g. summa canister 654) and an actuator (e.g. solenoid valve 656). The summa canister 654 may be a canister capable of being held at a vacuum or otherwise intaking a sample of air. In one example, the summa canister 654 is deployed with a vacuum contained therein. When the solenoid valve 656 is activated, a portion of atmosphere (air) is pulled into the summa canister 654. The action of the solenoid valve 656 may be remotely controlled or as illustrated connected to the pollution monitor 650 via a cable 658. From time to time, or during a leak event, the pollution monitor 650 may instruct the capture of a physical sample. In a similar manner, the physical sampling system 652 may be configured to capture and preserve a sample of water, a sample of fluid from the oil facility, a sample of soil, or other material as required.

In another alternative configuration, a method of collecting a physical sample may begin by provisioning a pollution monitor. Before provisioning, or at some point thereafter, at least one rule is established for invoking a sampling event. During regular operation of the atmosphere, the pollution monitor may be utilized to monitor for breach of the rule. If the rule is breached/met, the pollution monitor invokes to sample. The sample is captured with the physical sample and a location and/or time is attached to the sample. In some implementations, the physical sampling system 652 may be utilized as a one-time event. Alternatively, the physical sampling system 652 may draw in small samples over a period of time to determine a time-based average of pollution in the air. At a later point and (most likely) a different location, further analysis of the sampled air may help to identify the constituents of the air. For example, if the air contains a lot of propane, it its source is likely an oil and natural gas (O&NG) facility like a well or storage tank. Alternatively, if the air consists primarily of refined gasoline with additives, there might be a foul-running generator nearby that is simply emitting unspent gas as exhaust.

Therefore, the collection of samples are useful to classify the source through a detailed analysis. With this approach, external emissions sources may be disregarded without requiring laboratory grade analysis.

In another alternative configuration, a method of pricing natural gas may begin by monitoring an oil facility for a leak. Occasional leaks at the oil facility occur and timely and reliable repair are validated. If the repair is made timely and reliably, a clean certificate may be attached to a unit of natural gas. Sites with the fewest emissions may command the highest level of certification. This unit of natural gas with its attached clean certificate may be sold. Certain buyers of energy desire to have natural gas (or other extracted matter) that is sourced with minimal impact on the environment. Therefore, the market values certified clean matter at a higher rate than non-certified matter. This unit of natural gas with a clean certificate may create a new class of commodity with a premium price and/or a desirable market acceptance. Data integrity, security, and authentication may be of paramount importance to the accurate pricing of this commodity and methods may be applied to ensure that there is immutable, auditable, and complete ledger of the low carbon footprint of this product.

In another alternative configuration, a method of reporting quality of service of a repair at an oil facility may begin by installing a plurality of pollution monitors around an oil facility. A boundary may be established by connecting locations of the plurality of pollution monitors to define an on-site zone and an off-site zone. The pollution monitors may be used to detect a leak in the on-site zone; and, a technician located in the off-site zone may be moved to the on-site zone. The technician may repair the leak. The time to repair the leak may be noted; and, long-term effectiveness of the repair may be calculated. The time and effectiveness of the repair may be reported. The time and effectiveness may be used, for example, to confirm suitability of the repair technician.

In another alternative configuration, a method of subsidizing (at least some of) the purchase price of natural gas (by transacting a carbon credit), the process begins by baselining similar oil facilities to determine the typical emissions. The oil facility is monitored for a leak; and, all leaks are responded to. The response to leaks is validated. A carbon credit is attached to a unit of natural gas. The carbon credit may be transacted to a first buyer; and, the unit of natural gas may be transacted to a second buyer. The market has established frameworks for transacting (e.g. selling) matter with carbon credits attached thereto. The buyer of carbon credit containing units of natural gas maybe one user, or the buyer may opt to only purchase either the carbon credit or the unit of natural gas.

In another alternative configuration, a method of instructing another party to respond to a leak at an oil facility to cause transaction of a carbon credit, the process may begin by baselining similar oil facilities to determine the typical emissions. The oil facility is monitored for a leak; and, all leaks are responded to by another party. The response to leaks is validated. A carbon credit is attached to a unit of natural gas. The carbon credit may be transacted to a first buyer; and, the unit of natural gas may be transacted to a second buyer. Oil exploration, extraction, distribution, and processing is complicated and involves a number of parties. While the present illustrative examples attempt to narrow activities to the actions of one entity, various entities might perform actions. These actions may be taken on behalf of, or as instructed by, one party (e.g. the end consumer, the retailer, the producer, etc.).

In another alternative configuration, a method of confirming presence of a vehicle moving across an area populated with a plurality of pollution monitor may begin by providing a plurality of pollution monitors. The pollution monitors may monitor pollution sensors; and, when different pollution monitors validate identical atmosphere levels, a mobile emission source is identified. The presence of a mobile emission source is confirmed. Occasionally, a mobile emissions source such as a tractor may emit a large amount of hydrocarbons. This mobile emission source may cause false-positive reports of a leak at the oil facility. Therefore, identification of mobile emissions sources may be useful in confirming valid leaks.

In another alternative configuration, a method of validating a pollution event by analyzing a plurality of sensors and/or monitors for at least two breaches may begin with provisioning a pollution monitor having a variety of sensors. The presence of a leak may be validated by analyzing signals from the sensors by comparing signals from two or more sensors. While sensor and their associated signals may indicate leak events, it is useful to validate the leak before instructing to initiate actions (e.g. deploying a technician to the monitored area to repair a leak). Therefore, monitoring a plurality of sensors is useful.

In another alternative configuration, a method of adjusting communication frequency based on power budget may begin by monitoring the power input. The power stored in a battery is monitored. The telemetry is adjusted based on budget, actual and forecast power. The telemetry activities of a pollution monitor require a large amount of power, but the amount of data does not substantially change the amount of power required to report. Therefore, if charging conditions are diminished (e.g. low solar-resource days), the frequency of reporting can be adjusted.

Figure 38:
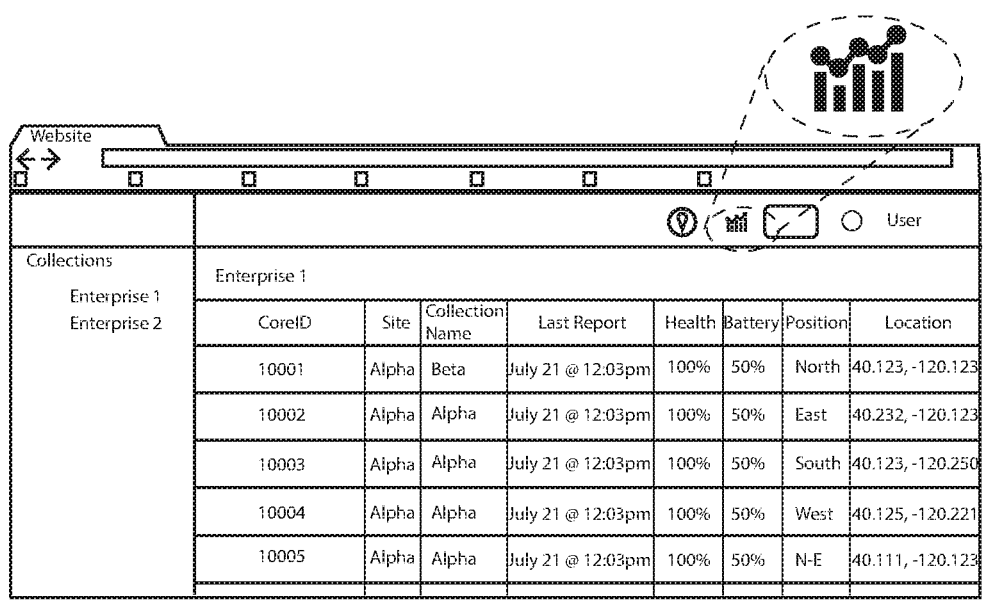
FIG. 38 is an information display, in data modality, configured as a website page served on the internet, according to an illustrative embodiment of the present disclosure.
Figure 39:
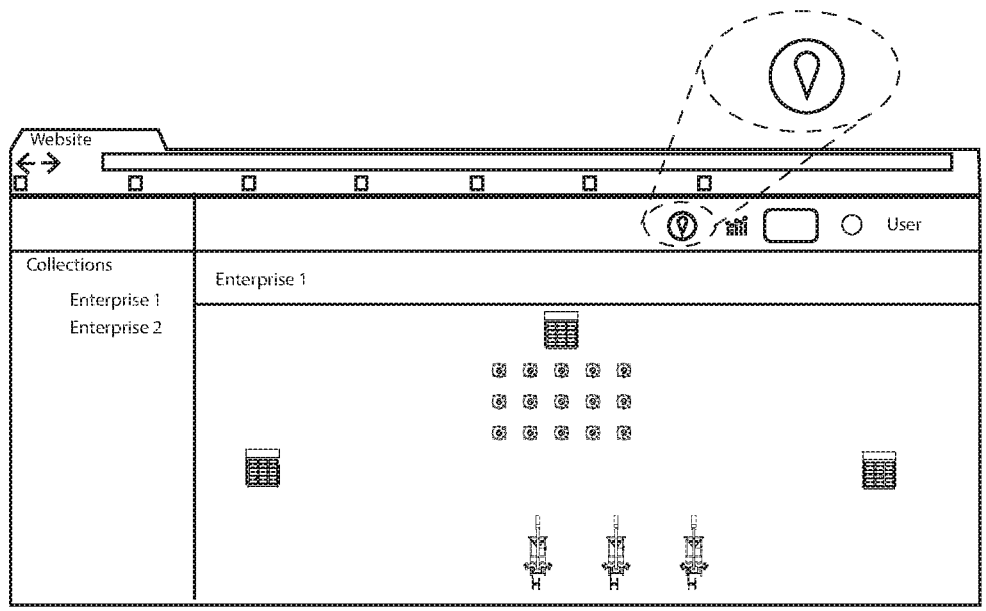
FIG. 39 is an information display, in map modality, configured as a website page served on the internet, according to an illustrative embodiment of the present disclosure.

In another alternative configuration, with reference to FIGS. 38 and 39 illustrating an information display in data modality and map modality, respectively, data from the pollution monitors may be configured as a website page served on the internet. Information received by the internet-attached web hosting server 420 (FIG. 32) via the communications tower 422 (FIG. 32) and the communications module 204 (FIG. 7) may be processed without any human interaction or influence. Alternatively, the data may be presented on a device, a webpage, a database, or any of a variety of other methods for receiving data. In one example, the data of one or more pollution monitors (e.g. 102) may be presented on a webpage that is updating at an interval. The updating interval may be so fast as to essentially be 'real time' or it may be every few hours (in one example it may be updated yearly). IoT data frequently needs some form of real-time dashboard. The present system utilizes a (custom-built or third-party) platform for illustrating the data in both a Data Modality (FIG. 38) and a Map Modality (FIG. 39). Creating and/or using these platforms facilitates rapid development and experimentation, for example, the granularity of data on the data modality of FIG. 38 can be adjusted. The data shown in the data modality (FIG. 38) may be at least one of the following: min, max, average pollution level (e.g. VoC), and time-series data that has been captured and/or processed by the electronics package 150. The data may be presented as realtime data, as spot-presented data, as summarized data, as max reading(s), as minimum reading(s) and/or as average data. Depending on the type of installation and required performance of the system, this data may be altered inside the electronics package 150, or the system (specifically one of the pollution monitors), or the internet-attached web hosting server 420, or on a local machine (not shown). In one embodiment, real time charts showing min, max, and average readings are provided in order to differentiate pollution monitors across an oil facility in order to monitor/watch for and analyze different readings. The map modality of FIG. 39 illustrates regional geospatial displays it may be appropriate to show individual devices. Data may be aggregated analyzed and summarized into a visual representation that enables the user to discern locations of interest. Drilling down from regional displays to more local geospatial areas may result in a different representation and a more fine-grained representation of the individual device data.

In another illustrative configuration, a method of communicating with property owners near an installation of a pollution monitor may begin by informing the neighboring property owners. The pollution monitor may be showed to at least one of the property owners. A link may be shared for public viewing of signals of the pollution monitor. The transparency of data from the method of communicating helps to avoid misunderstandings about the source of emissions.

In another alternative configuration, with reference to FIG. 40 illustrating a perspective view of one configuration of a pollution monitor 670, the pollution monitor 670 may be configured with an optional meteorological system (e.g. a wind sensor). The pollution monitor 670 may be provided with an air conveyance system 680. The air conveyance system 680 may include a tube 682 defining a sensor end 684 and an oppositely disposed collection end 688. The tube sensor end 684 may be attached to the electronics package housing 160 at the sensor opening 184 (FIG. 6). The tube collection end 688 may be positioned where the sampling should occur, for example as-illustrated on top of a body of water, or alternatively, down a borehole, on the top of a tank, inside a house, or wherever the ambient air may be monitored. The air conveyance system 680 may be further provided with a fan 690 fitted inline with the tube 682 for ensuring that the ambient air travels from the collection end 688 to the sensor end 684 of the tube 682. The fan 690 operates according to a set of predetermined inputs, intervals, or otherwise instructed by pre-programming, spot-programming or acquired intelligence. In many situations, air to be collected is located at a difficult location (e.g. the surface of a river, inside a holding tank, in a cave, underground in a drainage vault, etc). Often these difficult locations are subject to temporary flooding or are close to livestock or are prone to vandalism/theft. Therefore, providing a flowpath and conveyance from the difficult location to the environmental sensor is required. The hose 682 with a forced displacement device (e.g. the fan 690) may enable difficult locations to be monitored.

In another alternative configuration also shown in FIG. 40, the pollution monitor 670 may be provided with a meteorological module 700 configured to monitor any of a variety of environmental conditions. In one example, the meteorological module 700 may measure the humidity and/or the temperature of the air presented thereto. The meteorological module 700 may include a wind sensor 702 capable of measuring the speed and direction of the wind. The meteorological module 700 may further include features for measuring precipitation (rain, snow) or other conditions.

In another alternative configuration also shown in FIG. 40, the pollution monitor 670 may be provided with features for avoiding birds from interfering with the solar charging capabilities. For example, the pollution monitor 670 may be configured with a spike strip 710 attached to the top of the pollution monitor 670 as illustrated.

In another alternative configuration also shown in FIG. 40, the pollution monitor 670 may be configured with additional solar panels such as a second panel 720 and a third panel 730. The second panel 720 may be attached to a side of the pollution monitor 670 and the third panel 730 may be attached to the front of the pollution monitor 670.

In another alternative configuration shown in FIG. 32, the oil facility 100 may include four individual pollution monitors (e.g. 102, 104, 106, 108) or it may be provided with a relatively large number of pollution monitors (e.g. 280, 282, 284, 286). Regardless of the number of individual pollution monitors, they may communicate peer-to-peer (e.g. via a wireless mesh cellular network, via a proprietary network, or even via direct satellite transmission) or via the communications tower 422 and internet-attached web hosting server 420 via each environmental monitor system communications module 204 (FIG. 8). A few of the individual pollution monitors can be a centered cluster and further-away systems can be utilized to normalize or otherwise process data obtained by the systems. In a similar manner, a large string of data for each pollution monitor can be compared to as-measured readings in an effort to reduce false-positive events.

In another alternative configuration also shown in FIG. 32, the plurality of pollution monitors (102, 104, 106, 108, 280, 282, 284, 286) may communicate to time-average their baseline readings of the pollution sensor 202. Because the wind 410 is always changing direction and events are few and far between, over time, the readings of various pollution monitors can be evaluated (either manually or statistically) to arrive at an 'average' steady-state reading.

In another alternative configuration also shown in FIG. 32, the oil facility 100 houses the holding tanks 96 which may emit fluid (either gas or liquid) as the emissions source 400. If the emissions is hydrocarbons sourced from underground, the hydrocarbons may include many types of compounds. While methane is one particularly environment-degrading emissions, it is often emitted along with volatile organic compounds. In some, but not all, situations it is possible to estimate/measure methane emissions by measuring/sensing VOCs. As described herein, various sensors are capable of measuring VOCs such as micro hot-plate sensors. By sensing VOCs, the emission of methane can be estimated. The direct measurement of methane is relatively complex because methane is somewhat lighter than air, may be difficult to detect by nearly ground-level devices.

In another alternative configuration also shown in FIG. 32, the individual pollution monitors (102, 104, 106, 108, 280, 282, 284, 286) can communicate directly in a peer-to-peer manner via their individual LAN communications modules 208 (FIG. 8) where one pollution monitor may (or may not) communicate data to the internet-attached web hosting server 420 via the WAN communications module 210 of the pollution sensor 202. If implemented, this greatly reduces the power requirements of the oil facility 100 because communicating to nearby devices is substantially more energy efficient then communicating to distant devices.

In another alternative configuration, the pollution sensors may be configured with other and/or additional pollution sensors. For example, other pollution sensors cable of monitoring and/or reporting methane, particulates, volatile organic compound(s), etc. may be utilized. The pollution sensors may be any of a large variety of sensors, but in one configuration, the sensor module may be capable of sensing emissions from an oil extraction, storage, delivery, processing, and/or distribution component or system. Once such sensor is a volatile organic compound (VoC) sensor. Illustrative examples of sensors capable of sensing VOCs are temperature-controlled micro-hotplate devices such as the SGPC3 Sensirion Gas Platform made by Sensirion, www.sensirion.com. Another type of VOC sensor is an ultra-low power digital gas sensor for monitoring air quality that is manufactured by AMS and sold as model CCS811. The CCS811 is a digital gas sensor that integrates a metal oxide gas sensor to detect a wide range of VOCs using a micro-hotplate (also referred to herein as simply having a 'hotplate'). In yet another illustrative variant, pollution sensors may be a light-gate sensor wherein a light source creates light that is projected through air containing a gas (e.g. VOC such as Methane, Hexane, Toluene, Propane, Benzine, etc.) and received by a photodetector (e.g. ccd or cmos). The light received by the photodetector is processed and analyzed to determine constituents of the air through which the light passed. All of the sensors either present analog or digital information that indicates the presence of the component which it is intended to sense. In one example, the data is presented as binary data according to the 12C protocol well documented and known to those skilled in the art. This data is either processed by the electronics package 150 or transmitted to the cloud via the communications module 204 for later processing.

In another alternative configuration best illustrated in FIG. 15 illustrating one embodiment of a schematic diagram of optional power management devices of a pollution monitor (e.g. power switching, watchdog, etc), the electronics package 150 consumes power. Power may be provided by a grid-tied connection (not shown) or a battery 198. In most applications, the oil facility 100 is distant from the national grid and therefore the battery 198 is utilized and it is charged by the solar panel 140 (FIG. 3). With continued reference to FIG. 15, the electronics package 150 is, typically, capable of budgeting the daily power created by the solar panel 140 and stored in the battery 198. In typical mid-summer days, the sun's intensity causes excess power to be generated and operation can occur relatively frequently and with little regard for the amount of power consumed by the electronics package 150. Alternatively, in the middle of winter during a long period of foul weather, the electronics package 150 may need to reduce its overall power demands to compensate for the relatively low daily-power crated by the solar panel 140. The sampling cycle may be reduced during lower-power days (or periods) and/or the reporting of the data via the communications module 204 may be reduced as telemetry usually requires high amounts of power. In other words, the electronics package 150 and various components may be preprogrammed, spot-programmed, adapted by self or externally instructed to change performance to adapt to the power supplied to the device.

In another alternative configuration, the pollution monitors of the oil facility 100 may typically report according to a predetermined sampling interval (e.g. every 15-minutes). However, this sampling interval can be increased or decreased based on various conditions. Examples of sampling interval changing conditions include, but are not limited to, temperature, solar energy levels, battery status level, presence of an environmental event, etc. For example, if the temperature has been low and the solar energy levels are low, the oil facility 100 can be preconfigured or instructed to increase the time between sampling intervals to preserve battery levels. Alternatively, if one or more of the individual pollution monitors of the oil facility 100 detect an environmental event, the interval reading time may be increased (e.g. to every minute). In other words, the sampling interval can be dynamically controlled according to a predetermined set of rules or updated as needed.

In another alternative configuration, the solar panel 140 (FIG. 3) of the power system may be replaced by any of a variety of power supply/harvesting systems such as a thermo-voltaic power plant, a fuel cell, a large capacity battery, or grid-tied to the national grid via direct connection. These alternatives may or may not require the power management module 194 and/or the battery 198. Additionally, the battery 198 may be single-use or rechargeable chemistry.

In another alternative configuration, the electronics package 150 may include at least one status indicator 218 that is visual or auditory. For example, the enrolling step during installation may include a flashing LED (218, FIG. 8) on the electronics package 150 and/or a series of beeps that the installer can hear. These indicators (if provided) inform the installer about that status.

In another alternative configuration, the electronics package 150 may include a video recording module 220 for collecting, preserving and/or transmitting both stationery and video images of the monitored area 90.

In another alternative configuration, the electronics package 150 may include a proximity, orientation, movement module 222. If provided with this module/functionality, the location, orientation and any change in location can be collected, preserved and/or transmitted.

In another alternative configuration illustrated in FIG. 32, the individual pollution monitors (102, 104, 106, 108, 280, 282, 284, 286) can be configured according to a grid-pattern or as one or more concentric rings. The deployment and installation scheme is dictated by the type of monitoring to be accomplished and the topography of the oil facility 100.

In another alternative configuration illustrated in FIG. 33, the amplitude of a leak event and the duration of a leak event may inform a determination. With reference again to FIG. 33, for example, the amplitude of hydrocarbon emissions from pollution monitor 106 as well as the duration of the time (e.g. 50 minutes) may reduce false positive leak events. For example, if a hatch on a holding tank is opened for pumping of oil, this might cause hydrocarbons to be emitted for 50 minutes. Therefore, watching the amplitude and duration of a leak event may inform that this is a typical event at an oil facility and not a 'leak' that requires repair. By manually, automatically, or through artificial intelligence monitoring various events will help to learn what are normal operating events to avoid false alerts.

In another alternative configuration, the housing 160 may further include tapered walls to enable the parts to be nested for easy distribution. Additionally, the corners of the housing 160 may include water drainage holes 165 for ejecting water that may happen to enter the interior portion.

In another alternative configuration, the electronics package 150 may be configured using off-the-shelf hardware such as open-source platforms (e.g. Arduino) to enable integrated wireless communications without extensive firmware development. By using an integrated wireless microprocessors and Arduino-based hardware, the pollution monitor 108 may be efficiently updated.

In another alternative configuration, the pollution monitor may be minimized to a simple wedge-shaped structure wherein the insulating body 110 is a simple wedge housing an interior portion. A bird passage may be provided to result in this interior portion being capable of housing a bird. Or, the insulating body 110 may be configured as a panel mount of any type of configuration.

In another alternative configuration, with reference to FIG. 8, the logic control system 190 and/or the watchdog system 192 may be configured to receive data from the communications module 204 to enable over the air (OTA) updating. While the OTA packet may include only one number or letter of change, it may (alternatively) replace every line of code for operating the pollution monitor or its larger system. These changes may be configured as needed depending on the intended outcome. OTA updates enable management of large numbers of remotely deployed pollution monitors and enables on the fly adjustments.

In another alternative configuration, methods for statistically removing ambient levels of emissions are utilized for processing large quantities of data and filtering that data to remove potential falsely-reported leaks and other emission events results in a clean data set. Studying background levels informs data science approaches to identify sensors which may have drifted out of calibration. This study enables patterns to reveal importance of human activity, weather events/cycles, time-of-day and other external factors.

In another alternative configuration, the pollution sensors are automatically compensated as best described with reference to FIG. 6 wherein the pollution sensor 202 may 'drift' over time. If this change occurs, it may require baseline modification to adjust for the change (also referred to as 'drift'). The pollution sensor 202 may be comparted to other sensors in nearby pollution monitors (e.g. 104) and calculations can be made either onboard (e.g. via the logic control system 190) or remotely (e.g. internet-attached web hosting server 420, FIG. 32) to restore the functionality.

In another alternative configuration, pollution sensors that are designed for measuring one pollutant may have false-readings due to external conditions (e.g. metal oxide sensors may be sensitive to changes in humidity and temperature). While sensors may be programmed with onboard adjustment algorithms, the larger electronics package 150 may utilize other sensors (e.g. temperature, humidity, other sensors, etc.) to inform offsets that are due to environmental conditions verses those that are leak events.

In another alternative configuration, methods for aggregating bandwidth for cellular communications may be utilized as best described with reference to FIG. 32 wherein one or more of the communications modules (204, FIG. 15) may communicate with other nearby communication modules in other pollution monitors. This pollution monitor to pollution monitor communications may be referred to as peer-to-peer. In some instances, local communications may be all that is required as one of the pollution monitors may be 'online' (either fixed line or wirelessly). Alternatively, every third pollution monitor may include wireless communications to the internet-attached web hosting server 420 whereby one packet of data includes the readings from more than one pollution monitor. It should be apparent that by analyzing data consumption patterns of individual devices it may be possible to optimize the aggregation of data. In one illustrative embodiment, the various methods integrating wireless technologies to minimize bandwidth consumption, compression of specific data payloads, and adjustments to time of day and reporting frequency are all strategies to optimize the purchase of wireless bandwidth.

In another alternative configuration, database systems and architectures may be optimized for telemetry by utilizing non-conventional data storage techniques to optimize event storage. For example, rather than index in each row of data as it is stored (and possibly transmitted), indexing may be delayed until periods when telemetry streams are less congested. This reduces the bandwidth for transfer of traditional databases not designed for massive amounts of data.

In another alternative configuration, as best illustrated with reference to FIG. 38, another visualization tool may be provided to facilitate rapid dashboard implementation techniques beyond map modality and data modality. This expanded visualization tool may be employed to illustrate anomalies and the impact of a myriad of meteorological and environmental factors (that may include advanced statistical and visual representations).

In another alternative configuration, the pollution monitor and associated system(s) may be configured a business model where data is sold as a service. While some implementations of the described embodiment(s) may be simple cash-sales, others may be provided under a service agreement. Wherein the system is a service agreement, the service provider will handle the procurement of the pollution monitor(s) and/or deployment of the pollution monitor to the field. The recipient of the benefits and/or data will be invoiced and obligated to pay for the services. In one example, this will be a daily fee and, in another example, it will be an annual fee. The costs for this benefit may be born as a form of reparation for individuals or environment damaged by prior emissions, or the cost my be paid by municipalities.

In another alternative configuration, data science may be utilized to facilitate remote re-calibration of various components of a pollution monitor, or the larger system. Over time and with a large number of pollution monitors deployed, a large set of data will be developed. This dataset may be useful in reducing false-positives of leaks and/or remote calibration of sensors capable of adapting over time.

In another alternative configuration, the clean certificate may be created in-whole or in-part by an internal genesis block chain creation with a unique blockchain per pollution monitor. Each pollution monitor may uniquely derive a genesis block internally with its own microprocessor. Each pollution monitor may then produce its own blocks such that each canary will produce its own unique blockchain. The genesis block may be produced based on location (e.g. GPS data), hardware serial numbering (e.g. MAC address), baseline sensor data, and the other parameters. Furthermore, the blockchain hierarchy may be generated by each pollution monitor that may feed into different levels of blockchains. A first level may be a single pollution monitor blockchain. A second level may be a site (i.e. a first collection of pollution monitor), A second level may be a field (i.e. a second collection of pollution monitor that may include the first collection). A third level may be a basin (i.e. a third collection of canaries that may include the first and/or second collection. A fourth level may be a company. Each higher level blockchain may employ a smart contract or some other means to take as input blocks from lower level blockchains. For example, a company level blockchain may receive information from multiple basin blockchains associated with that company. Thus, the audit trail may follow several different blockchains.

In another alternative configuration, different levels of privatization of one or more components of a blockchain may be controlled through encryption. A company may want to keep data related to its pollution private until they clean up their act. Thus, a company may determine via encryption, access control lists, and the like, which parts of a blockchain are public. However, even if data is encrypted the trail of data may still be auditable. In one embodiment, a result of data within the blockchain may be made public, for example the measured PPM data may be encrypted but the resulting status of green, yellow, red may be made public, which identifies the current status of a particular site, basin, canary, and the like.

In another alternative configuration, certification of specific blockchain may be according to rules on what it takes to be certified may be public and stored in the blockchain. The rules may be based on geochemistry of each site. The certification specific blockchain may take as inputs sensor data from one or more sites and may rank those sites according to the public rules and output the rankings of those sites. The rankings may be dynamic in nature. The input into the certification specific blockchain may be a smart contract that only takes blockchain data from predetermined lower level blockchains. For example, data accepted by the certification specific blockchain may have to be from one or more registered sites.

In another alternative configuration, synch metrics may be modified whereby sampling frequency across pollution monitors may vary based on different events. For example, when a first pollution monitor detects a reading above pre-established noise-level then it may signal to neighboring pollution monitors to start sampling more frequently since it is likely a leak is happening. If pollution monitor are solar powered, they may reduce or increase frequency of sampling based on remaining power and/or weather forecast.

In another alternative configuration, an olfactory monitor may improve public relations and help to mitigate climate change through a process of creating a base-line reading and then monitoring for breach of the base-line reading. A pollution monitor may be provided with a pollution sensor (for example, a hydrocarbon sensor having a heat plate) to monitor and report foul-emissions that impact adjacent properties including a communications system for notifying a service company to deploy a repair crew. Pollution monitors may be utilized by home oil companies and homeowners alike (e.g. homeowners by oil facilities). The certification specific blockchain may take as an input canary produced blockchains at home locations to determine if there is an indecent within a particular neighborhood. This may be useful to determine "safe" neighborhoods and the like. Once it is determined that a particular site has breached a base-line (i.e. noise level) various actions may be taken by a canary within that site, such as initializing a microphone, taking one or more still pictures, sending alerts, open a summa canister (for sampling), and the like. These actions and the results of these actions may be saved in the blockchain for an audit trail.

In another alternative configuration, the pollution monitor and associated system(s) may be configured with a seismic event sensor (e.g. an accelerometer or other device utilized for indicating a seismic event). By accurately timing (e.g. via the GPS clock time) the arrival of a seismic event at each monitor, the location of the seismic event may be determined.

In another alternative configuration shown in FIGS. 41 to 47, an illustrative ornamental appearance of a pollution monitor may include an optional vertical object and other narrow aesthetic details. It is to be understood that features may be claimed as environmental features or simply removed to refine various embodiments of the present disclosure.

In another alternative configuration shown in FIGS. 48 to 56, an illustrative ornamental appearance of a pollution monitor may include optional (a narrow) aesthetic details. It is to be understood that features may be claimed as environmental features or simply removed to refine various embodiments of the present disclosure.

While the above description includes terms such as top, bottom, left, right, inside, outside, front, back, and other descriptors regarding physical orientation and/or position, it is to be understood that these are provided for illustrative purposes only. It is to be understood that the orientation of the pollution monitor 108 can be changed and the various descriptions may be confusing. However, the present description was provided to convey to one skilled in the art the embodiment(s).

While the principles of the disclosure have been described above in connection with the specific apparatuses and methods, it is to be understood that this description is made only by way of example and not as limitation on the scope of the disclosure.

What is claimed is:

1. A pollution monitor for an oil facility comprising:
a housing comprising:
an interior;
an exterior;
a first venturi opening formed in the housing configured to allow airflow between the exterior and interior;
a second venturi opening formed in the housing configured to allow airflow between the interior and exterior; and
an airstream path in the interior between the first venturi opening and the second venturi opening;
an electronics package positioned in the interior of the housing adjacent to the airstream path, the electronics package comprising:
a pollution sensor electrically interfaced with the electronics package and configured to output a signal representative of an airborne pollutant concentration; and
a communications circuit electrically interfaced with the electronics package and configured to transmit the airborne pollutant concentration;
a panel mount attached to the housing comprising
a top configured at
a pitch angle formed between the top and a global-horizontal plane, wherein the pitch angle is greater than zero degrees;
a solar panel:
attached to the top of the panel mount,
electrically interfaced with the electronics package, and
configured to drain water and to increase solar charging;
an expansion connector formed on the exterior of the housing and in electrical communication with the electronics package; and
a power conductor:
electrically interfaced with the solar panel,
electrically interfaced with the electronics package, and
passing through the housing.

2. The pollution monitor of claim 1, wherein the expansion connector is a telecommunications registered jack.

3. The pollution monitor of claim 1 and further comprising:
a physical sampling system:
attached to the expansion connector,
in electrical communication with the electronics package, and
configured to flow a sample of air into the physical sampling system.

4. The pollution monitor of claim 3 wherein the pollution monitor is configured to capture and preserve the sample of air with the physical sampling system.

5. The pollution monitor of claim 1 and further comprising:
a metrological connector electrically interfaced with the electronics package and configured to receive data representative of at least one meteorological condition.

6. The pollution monitor of claim 5 and further comprising:
a metrological circuit electrically interfaced with the metrological connector and configured to output a signal representative of direction of wind.

7. The pollution monitor of claim 1 wherein the panel mount further comprises:
an insulating body configured to reduce heat transfer from the solar panel to the electronics package.

8. The pollution monitor of claim 7 wherein the insulating body further comprises:
a wood portion; and
wherein the housing is attached to the wood portion.

9. The pollution monitor of claim 1 wherein the panel mount further comprises:
a box comprising:
an interior; and
an exterior; and
a bird passage formed in the box and configured to provide physical passage for a bird between the interior and the exterior.

10. The pollution monitor of claim 1 wherein the pitch angle is between 15 degrees and 55 degrees.

11. The pollution monitor of claim 1 and further comprising:
a brim parallel to the first venturi opening, the brim configured to block rain from entering the interior via the first venturi opening;
an airgap located between the venturi opening and the brim; and
wherein the airgap is in fluid communication with the interior and the exterior.

12. The pollution monitor of claim 1 and further comprising:
a vertical object anchored to ground; and
a fastener configured to attach the pollution monitor to the vertical object.

13. The pollution monitor of claim 12 wherein the vertical object further comprises:
an elongated member:
having a uniform cross-section, and
at least three feet long.

14. The pollution monitor of claim 13 wherein the elongated member further comprises:
a spade formed on a proximal end of the elongated member; and
an anvil formed on a distal end of the elongated member.

15. A method for sampling air pollution at an oil facility comprising:
providing a pollution monitor comprising:
a housing configured to receive one or more components and to protect the components from outdoor environmental conditions;
an electronics package disposed in the housing, wherein the electronics package determines a location using trilateration;
a pollution sensor in electrical communication with the electronics package, the pollution sensor configured to output a signal representative of a pollutant concentration; and
a physical sampling system in electrical communication with the electronics package, wherein the physical sampling system is coupled to the pollution monitor using an expansion connector attached to the housing;
establishing a rule for invoking a sampling event;
monitoring for breach of the rule;
invoking, upon breach of the rule, the pollution monitor to initiate sampling; and
sampling air pollution by:
capturing a sample of air with the physical sampling system; and
storing the location of the sample of air.

16. The method for sampling of claim 15 wherein the providing the pollution monitor further comprises providing:
a real-time clock in electrical communication with the electronics package; and
wherein the sampling air pollution further comprises:
storing the time of the sample of air.

17. The method for sampling of claim 15 and further comprising:
energizing the physical sampling system during the sampling.

18. The method for sampling of claim 17 and further comprising:
wherein the energizing the physical sampling system comprises energizing a solenoid during sampling.

19. A pollution monitor for an oil facility comprising:
a housing comprising:
an interior;
an exterior;
a first venturi opening formed in the housing configured to allow airflow between the exterior and interior;
a second venturi opening formed in the housing configured to allow airflow between the interior and exterior; and
an airstream path in the interior between the first venturi opening and the second venturi opening;
an electronics package positioned in the interior of the housing adjacent to the airstream path, the electronics package comprising:
a pollution sensor electrically interfaced with the electronics package and configured to output a signal representative of an airborne pollutant concentration; and
a communications circuit electrically interfaced with the electronics package and configured to transmit the airborne pollutant concentration:
a panel mount attached to the housing comprising a top configured at a pitch angle formed between the top and a global-horizontal plane, wherein the pitch angle is greater than zero degrees;
a solar panel:
attached to the top of the panel mount,
electrically interfaced with the electronics package, and
configured to drain water and to increase solar charging; and
a power conductor:
electrically interfaced with the solar panel,
electrically interfaced with the electronics package, and
passing through the housing:
a vertical object configured for anchoring to ground;
a fastener configured to attach the pollution monitor to the vertical object,
an elongated member:
having a uniform cross-section, and
at least three feet long;

a spade formed on a proximal end of the elongated member; and an anvil formed on a distal end of the elongated member.

20. The pollution monitor of claim 19, further comprising an expansion connector formed on the exterior of the housing and in electrical communication with the electronics package.

* * * * *